United States Patent
Heidmann

(10) Patent No.: US 9,482,612 B2
(45) Date of Patent: Nov. 1, 2016

(54) PHOTON EMITTER CHARACTERIZATION USING PHOTOLUMINESCENCE QUENCHING IN NITROGEN VACANCY COLOR CENTERS

(71) Applicant: Infinitum Solutions, Inc., Santa Clara, CA (US)

(72) Inventor: Juergen Heidmann, Salinas, CA (US)

(73) Assignee: Infinitum Solutions, Inc., Santa Clara, CA (US)

( * ) Notice: Subject to any disclaimer, the term of this patent is extended or adjusted under 35 U.S.C. 154(b) by 0 days.

(21) Appl. No.: 14/542,410

(22) Filed: Nov. 14, 2014

(65) Prior Publication Data
US 2016/0139048 A1    May 19, 2016

(51) Int. Cl.
G01N 21/63    (2006.01)

(52) U.S. Cl.
CPC ..... *G01N 21/63* (2013.01); *G01N 2201/06113* (2013.01)

(58) Field of Classification Search
CPC ............. G01N 21/6458; G01N 21/6428; G01N 24/00
See application file for complete search history.

(56) References Cited

U.S. PATENT DOCUMENTS

| | | | |
|---|---|---|---|
| 5,770,856 A | 6/1998 | Fillard et al. | |
| 6,259,104 B1 | 7/2001 | Baer | |
| 6,389,210 B1 | 5/2002 | Mukasa et al. | |
| 6,891,151 B2 | 5/2005 | Shimada et al. | |
| 7,305,869 B1 | 12/2007 | Berman et al. | |
| 7,861,316 B2 | 12/2010 | van der Weide et al. | |
| 8,193,808 B2 | 6/2012 | Fu et al. | |
| 8,415,640 B2 | 4/2013 | Babinec et al. | |
| 8,455,278 B2 | 6/2013 | Linares et al. | |
| 8,547,090 B2 | 10/2013 | Lukin et al. | |
| 8,885,301 B1 | 11/2014 | Heidmann | |
| 2010/0308813 A1* | 12/2010 | Lukin et al. | ............... 324/244.1 |

(Continued)

FOREIGN PATENT DOCUMENTS

WO    WO 2014/051886 A1    4/2014

OTHER PUBLICATIONS

Lai et al., "Quenching nitrogen—vacancy center photoluminescence with an infrared pulsed laser", 2013 New J. Phys. 15033030, http://iopscience.iop.org/1367-2630/15/3/033030.*

(Continued)

*Primary Examiner* — Marcus Taningco
(74) *Attorney, Agent, or Firm* — Silicon Valley Patent Group LLP

(57) ABSTRACT

A crystal film with nitrogen vacancy centers is placed in close proximity to a photon emitter. Excitation illumination is produced to cause the nitrogen vacancy centers to produce photoluminescence. Illumination is produced by the photon emitter, which may be near field or far field and which quenches the photoluminescence intensity using an effect known as Stimulated Emission Depletion (STED). The quenching caused by the photon emitter is detected and analyzed to determine characteristics of the photon emitter. The analysis takes into account the characteristic dependence of the STED on the depletion light power, i.e. the photon source, and a spatial distribution of the light intensity. The analysis may be applied to spatially resolved measurements or an integral value of the photoluminescence quenching. The analysis may determine characteristics such as peak power, power scaling factor, and FWHM of the illumination profile of the photon emitter.

38 Claims, 10 Drawing Sheets

(56) References Cited

U.S. PATENT DOCUMENTS

| | | |
|---|---|---|
| 2012/0019242 A1 | 1/2012 | Hollenberg et al. |
| 2013/0032734 A1* | 2/2013 | Santori et al. ............. 250/458.1 |
| 2014/0166904 A1 | 6/2014 | Walsworth et al. |
| 2015/0235661 A1 | 8/2015 | Heidmann |
| 2015/0253355 A1 | 9/2015 | Grinolds et al. |

OTHER PUBLICATIONS

Challener et al. "Near-field optics for heat-assisted magnetic recording (experiment, theory, and modeling)," *Modelling and Numerical Simulations II*, Modern Aspects of Electrochemistry 44:53-110, 2009.

Chen et al. "Sub-diffraction optical manipulation of the chargestate of nitrogen vacancy center in diamond", ArXiv e-prints, 21 pages, 2014.

Chernyshov et al. "Measurement of Magnetic Properties Relevant to Heat-Assisted-Magnetic-Recording", *IEEE Transactions on Magnetics* 49(7):3572-3575, 2013.

Chmyrov et al. "Nanoscopy with more than 100,000 'doughnuts'" *Nature Methods* 10(8):737-743, 2013.

Han et al. "Three-Dimensional Stimulated Emission Depletion Microscopy of Nitrogen-Vacancy Centers in Diamond Using Continuous-Wave Light", *Nano Lett* 9(9):3323-3329, 2009.

Hao et al. "Effects of polarization on the de-excitation dark focal spot in STED microscopy," *Journal of Optics* 12(11):115707-1-8, 2010.

Moneron et al. "Two-photon excitation STED microscopy," *Opt Express* 17(17):14567-14573, 2009.

Rittweger et al. "Far-field fluorescence nanoscopy of diamond color centers by ground state depletion," EPL (*Europhysics Letters*) 86(1):14001, 2009.

Rittweger, E. et al. "STED microscopy reveals crystal colour centres with nanometric resolution," *Nature Photonics* DOI:10.1038/NPHOTON.2009.2:1-4, 2009.

Rottmayer et al. "Heat-Assisted Magnetic Recording," *IEEE Trans Magnetics* 42(10):2417-2421, 2006.

Schrof et al. "STED nanoscopy with mass-produced laser diodes," *Optics Express* 19(9): 8066-8072, 2011.

Seigler et al. "Integrated Heat Assisted Magnetic Recording Head: Design and Recording Demonstration," *IEEE Trans Magnetics* 44(1):119-124, 2008.

Vicidomini et al. "STED Nanoscopy with Time-Gated Detection: Theoretical and Experimental Aspects," *Plos One* 8(1):e54421:1-12, 2013.

Wang et al. "Time-gated STED nanoscopy," located at http://www.paper.edu.cn, p. 1-8, 2013.

Willig et al. "STED microscopy with continuous wave beams," *Nat Meth* 4(11):915-918, 2007.

Choy, J. et al. (May 20, 2011). Enhanced Single Photon Emission from a Diamond-Silver Aperture, arXIV:1105.4096v1 [*quant-ph*] p. 1-16.

Doherty, M. et al. (Oct. 28, 2013). "The temperature shifts of the resonances of the NV-center in diamond," arXiv:1310.7303v1 [*cond-mat.mtrl-sci*] p. 1-6.

Epstein, R. et al. (2005). "Anisotropic interactions of a single spin and dark-spin spectroscopy in diamond," Center for Spintronics and Quantum Computation, University of California, Santa Barbara, CA, p. 1-17.

Fuchs, G. et al. (Jun. 11, 2008). "Excited-state spectroscopy using single-spin manipulation in diamond," arXiv:0806.1939v1 [*quant-ph*] p. 1-15.

Greffet, J.-J. et al. (Jul. 3, 2011). "Diamond particles as nanoantennas for nitrogen-vacancy color centers," arXiv:1107.0502v1 [*physics.optics*] p. 1-4.

Grinolds, M. et al. (Sep. 2, 2012). "Nanoscale magnetic imaging of a single electron spin under ambient conditions," arXiv:1209.0203v1 [*cond-mat.mes-hall*] p. 1-12.

Grinolds. (2014). "Nanoscale Magnetic Resonance Imaging and Magnetic Sensing Using Atomic Defects in Diamond," PhD thesis. Harvard University: Cambridge, Massachusetts, 152 pages.

Gruber, A. et al. (1997). "Scanning Confocal Optical Microscopy and Magnetic Resonance on Single Defect Centers," *Science* 276: 2012.

Han, K. et al. (Jul. 22, 2010). "Metastable Dark States Enable Ground State Depletion Microscopy of Nitrogen Vacancy Centers in Diamond with Diffraction-Unlimited Resolution," *Nano Lett 10*: 3199-3203.

Hausmann, B. et al. (Apr. 5, 2011). "Single-color centers implanted in diamond nanostructures," *New Journal of Physics* 13(045004):1-11.

Hong, S. et al. (Feb. 8, 2012). "Coherent, mechanical control of a single electronic spin," arXiv:1202.1823v1 [*cond-mat.mes-hall*] p. 1-6.

Horowitz, V. et al. (Jun. 7, 2012). "Electron spin resonance of nitrogen-vacancy centers in optically trapped nanodiamonds," arXIV:1206.1573v1 [*cond-mat.mtrl-sci*] p. 1-29.

Kucsko, G. et al. (Apr. 3, 2013). "Nanometer scale quantum thermometry in a living cell," arXIV:1304.1068v1 [*quant-ph*] p. 1-22.

Lai, N. et al. (Sep. 8, 2009). "Influence of a static magnetic field on the photoluminescence of an ensemble of Nitrogen-Vacancy color centers in a diamond single-crystal," arXiv:0908.1327v2 [*cond-mat.mtrl-sci*] p. 1-4.

Laraoui, A. et al. (May 7, 2013). "High-Resolution Correlation Spectroscopy of 13C Spins Near a Nitrogen-Vacancy Center in Diamond," arXiv:1305.1536v1 [*cond-mat.mes-hall*] p. 1-22.

Le Sage et al. (2012). "Efficient Photon Detection from Color Centers in a Diamond Optical Waveguide," *Physical Review B* 85:121202-1-4.

Lesik, M. et al. (Jan. 13, 2014). "Perfect preferential orientation of nitrogen-vacancy defects in a synthetic diamond sample," arXiv:1401.2795v1 [*cond-mat.mtrl-sci*] p. 1-6.

Maclaurin, D. et al. (Jul. 23, 2012). "Nanoscale magnetometry through quantum control of nitrogen-vacancy centres in rotationally diffusing nanodiamonds," arXIV:1207.5276v1 [*quant-ph*] p. 1-9.

Malentinsky, P. et al. (Aug. 22, 2011). "A robust, scanning quantum system for nanoscale sensing and imaging," arXiv:1108.4437v1 [*cond-mat.mes-hall*] p. 1-11.

Maletinsky. (2012). "A Robust Scanning Diamond Sensor for Nanoscale Imaging with Single Nitrogen-Vacancy Centres," *Nature Nanotechnology* vol. 7: 320-324.

Mamin, H. et al. (Feb. 1, 2013). "Nanoscale Nuclear Magnetic Resonance with a Nitrogen-Vacancy Spin Sensor," *Science* 339: 557-560.

Mamin, H. et al. (Sep. 14, 2012). "Detecting External Electron Spins Using Nitrogen-Vacancy Centers," IBM Research Division, Almaden Research Center, San Jose, CA, p. 1-25.

Meijer, J. et al. (May 1, 2008). "Towards the implanting of ions and positioning of nanoparticles with nm spatial resolution," *Appl Phys. A* 91:567-571.

Michl, J. et al. (Jan. 16, 2014). "Perfect alignment and preferential orientation of nitrogen-vacancy centers during CVD growth on (111) surfaces," arXiv:1401.4106v2 [*cond-mat.mes-hall*] p. 1-6.

Neumann, P. et al. (Apr. 2, 2013). "High precision nano scale temperature sensing using single defects in diamond,"arXIV:1304.0688v1 [*quant-ph*] p. 1-6.

Pham, L. et al. (Apr. 28, 2011). "Magnetic field imaging with nitrogen-vacancy ensembles," *New Journal of Physics* 13(045021):1-13.

Rondin, L. et al. (Apr. 13, 2012). "Nanoscale magnetic field mapping with a single spin scanning probe magnetometer," arXiv:1108.4438v3 [*cond-mat.mes-hall*] p. 1-10.

Schirhagl, R. et al. (Nov. 12, 2013). "Nitrogen-Vacancy Centers in Diamond: Nanoscale Sensors for Physics and Biology," *Annu. Rev. Phys. Chem.* 2014(65):83-105.

Taylor et al. (2008). "High-Sensitivity Diamond Magnetometer with Nanoscale," *Nature Physics* vol. 4:810-816.

(56) References Cited

OTHER PUBLICATIONS

Taylor, J. et al. (May 9, 2008). "High-sensitivity diamond magnetometer with nanoscale resolution," arXiv:0805.1367v1 [*cond-mat.mes-hall*] p. 1-29.

Tetienne, J-P. (Oct. 19, 2012). "Magnetic-field dependent photodynamics of single NV defects in diamond: An application to qualitative all-optical magnetic imaging," *New Journal of Physics* 14(103033):1-15.

Toyli, D. et al. (Jul. 16, 2012). "Measurement and control of single nitrogen-vacancy center spins above 600K," arXIV:1201.4420v2 [*cond-mat.mes-hall*] p. 1-22.

Toyli, D. et al. (Jul. 23, 2010). "Chip-Scale Nanofabrication of Single Spins and Spin Arrays in Diamond," *Nano Lett* 10:3168-3172.

Toyli, D. et al. (Mar. 27, 2013). "Fluorescence thermometry enhanced by the quantum coherence of single spins in diamond," arXIV:1303.6730v2 [*cond-mat.mes-hall*] p. 1-15.

U.S. Appl. No. 14/952,852 filed on Nov. 25, 2015 by Infinitum Solutions, Inc., 61 pages.

Wrachstrup et al. (2009). "Single Spins in Diamond-Probes for Nanoscience," Molecular Imaging, Cornell University, Ithaca, p. 1-27.

\* cited by examiner

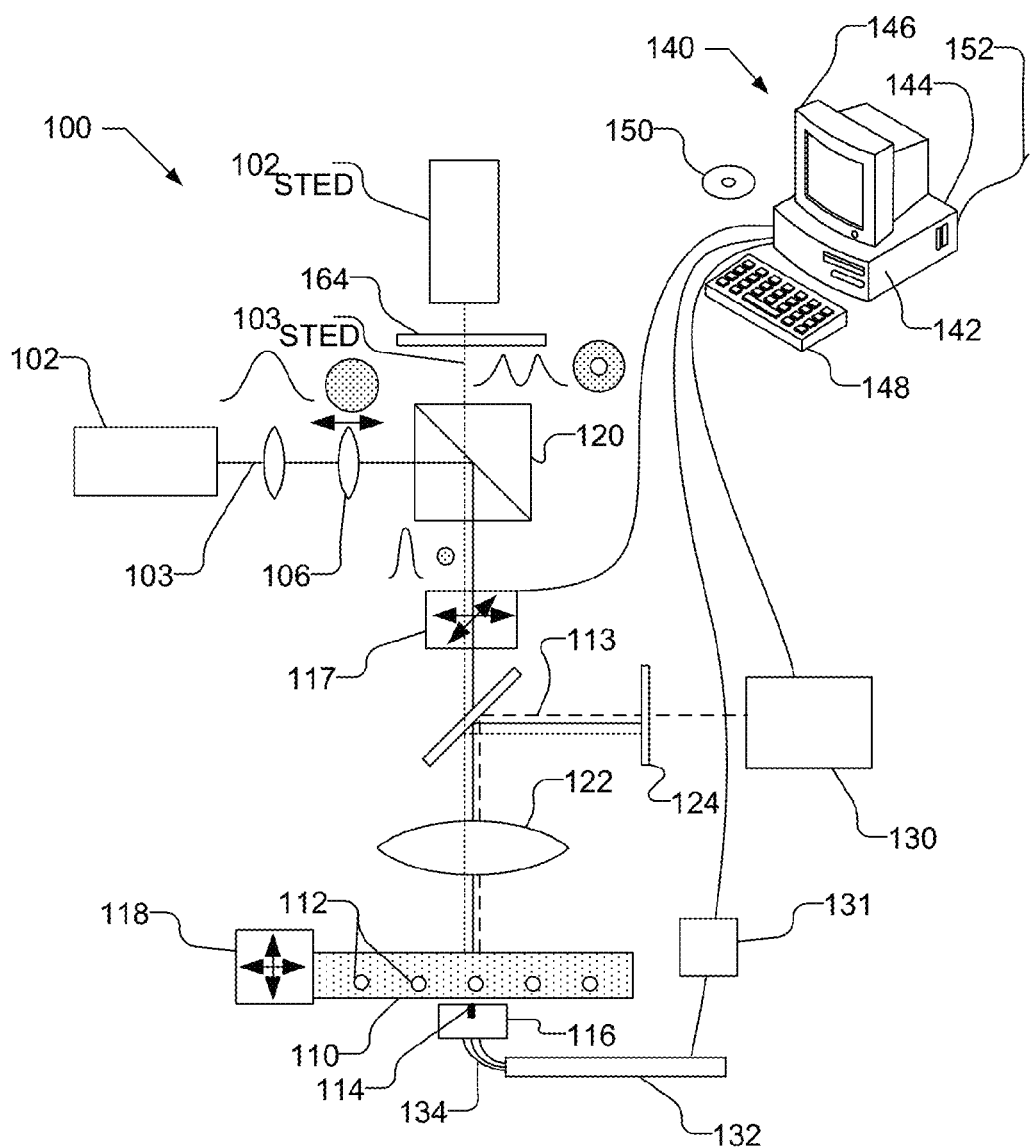
Fig. 12
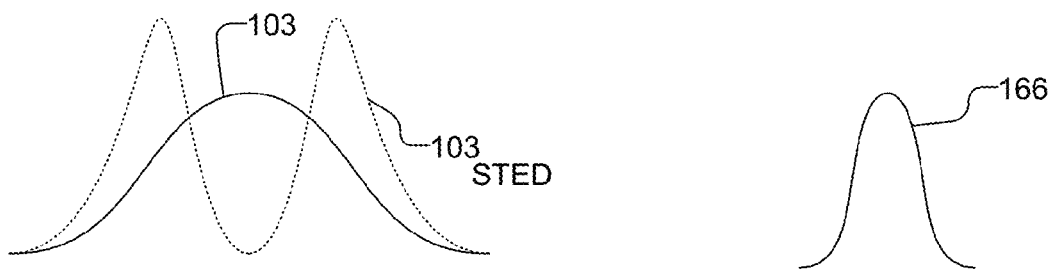
Fig. 13
Fig. 14

PHOTON EMITTER CHARACTERIZATION USING PHOTOLUMINESCENCE QUENCHING IN NITROGEN VACANCY COLOR CENTERS

BACKGROUND

Photon emitters that produce near field illumination are sometimes used in, e.g., magnetic recording heads, in which the photon emitter is used to heat the recording medium. For example, near field photon emitters are used in heat assisted magnetic recording (HAMR). Other applications of near field photon emitters include, e.g., optical fibers, plasmon tips for optical near field microscopy (SNOM), nano-photonics devices, optical wave-guides, and laser-diodes. Characterization of such near field photon emitters, such as the size of the aperture or power, is useful. Additionally, characterization of far field photon emitters, such as the beam waist of a focused laser may be useful. Accordingly, an improved metrology method for characterizing photon emitters is desired.

SUMMARY

A crystal film with nitrogen vacancy centers is placed in close proximity to a photon emitter. Excitation illumination is produced to cause the nitrogen vacancy centers to produce photoluminescence. Illumination is produced by the photon emitter, which may be near field or far field and which quenches the photoluminescence intensity using an effect known as Stimulated Emission Depletion (STED). The quenching caused by the photon emitter is detected and analyzed to determine characteristics of the photon emitter. The analysis takes into account the characteristic dependence of the STED of the crystal film with nitrogen vacancy centers on the depletion light power, i.e. the photon source, and a spatial distribution of the light intensity. The analysis may be applied to spatially resolved measurements or an integral value of the photoluminescence quenching. The analysis may fitting to a model or comparing to a library and determines characteristics such as peak power, power scaling factor, and FWHM of the illumination profile of the photon emitter.

In one implementation, a method of determining one or more characteristics of a photon emitter includes producing excitation illumination that is incident on a crystal film with one or more nitrogen vacancy centers, wherein the one or more nitrogen vacancy centers produces photoluminescence with an intensity in response to the excitation illumination; producing illumination from the photon emitter, the illumination being incident on the crystal film with the one or more nitrogen vacancy centers, wherein the illumination produced by the photon emitter quenches the intensity of the photoluminescence from the one or more nitrogen vacancy centers; detecting an amount of quenching of the intensity of the photoluminescence from the one or more nitrogen vacancy centers caused by the illumination of the photon emitter; and analyzing the amount of quenching of the intensity of the photoluminescence to determine the one or more characteristics of the photon emitter.

In one implementation, a method of determining one or more characteristics of a photon emitter includes producing a first excitation illumination that is incident on a crystal film with one or more nitrogen vacancy centers, wherein the one or more nitrogen vacancy centers produces photoluminescence with an intensity in response to the first excitation illumination; detecting a first photoluminescence intensity from the one or more nitrogen vacancy centers in response to the first excitation illumination; producing a second excitation illumination that is incident on the crystal film with the one or more nitrogen vacancy centers; producing illumination from the photon emitter, the illumination being incident on the crystal film with the one or more nitrogen vacancy centers, wherein the illumination produced by the photon emitter quenches the intensity of the photoluminescence produced by the one or more nitrogen vacancy centers in response to the second excitation illumination; detecting a second photoluminescence intensity from the one or more nitrogen vacancy centers in response to the second excitation illumination and the illumination produced by the photon emitter; determining an amount of quenching of photoluminescence intensity based on a difference between the first photoluminescence intensity and the second photoluminescence intensity; and analyzing the amount of quenching of the photoluminescence intensity to determine the one or more characteristics of the photon emitter.

In one implementation, an apparatus for determining one or more characteristics of a photon emitter includes a light source that produces excitation illumination that is incident on a crystal film with one or more nitrogen vacancy centers, wherein the one or more nitrogen vacancy centers produces photoluminescence with an intensity in response to the excitation illumination; a microscope configured to detect the photoluminescence produced by the nitrogen vacancy centers in response to the excitation illumination; a bias source configured to provide bias signals; a probe card coupled to the bias source and configured to be connected to a device that includes the photon emitter, the probe card provides a bias signal to the device that causes the photon emitter to emit illumination that is incident on the crystal film with the one or more nitrogen vacancy centers, wherein the illumination produced by the photon emitter quenches the intensity of the photoluminescence from the one or more nitrogen vacancy centers; and a processor coupled to control the microscope, the light source and the bias source and configured to cause the microscope to detect the photoluminescence produced by the nitrogen vacancy centers in response to the excitation illumination and to determine an amount of quenching of the intensity of the photoluminescence from the one or more nitrogen vacancy centers caused by the illumination of the photon emitter, and to analyze the amount of quenching of the intensity of the photoluminescence to determine the one or more characteristics of the photon emitter.

BRIEF DESCRIPTION OF THE DRAWINGS

FIG. 12 illustrates an optical metrology device that uses Stimulated Emission Depletion (STED).

FIG. 13 illustrates the point spread function of excitation illumination and STED illumination.

FIG. 14 illustrates the effective point spread function of the combined excitation illumination and STED illumination from FIG. 13.

DETAILED DESCRIPTION

Figure 1:
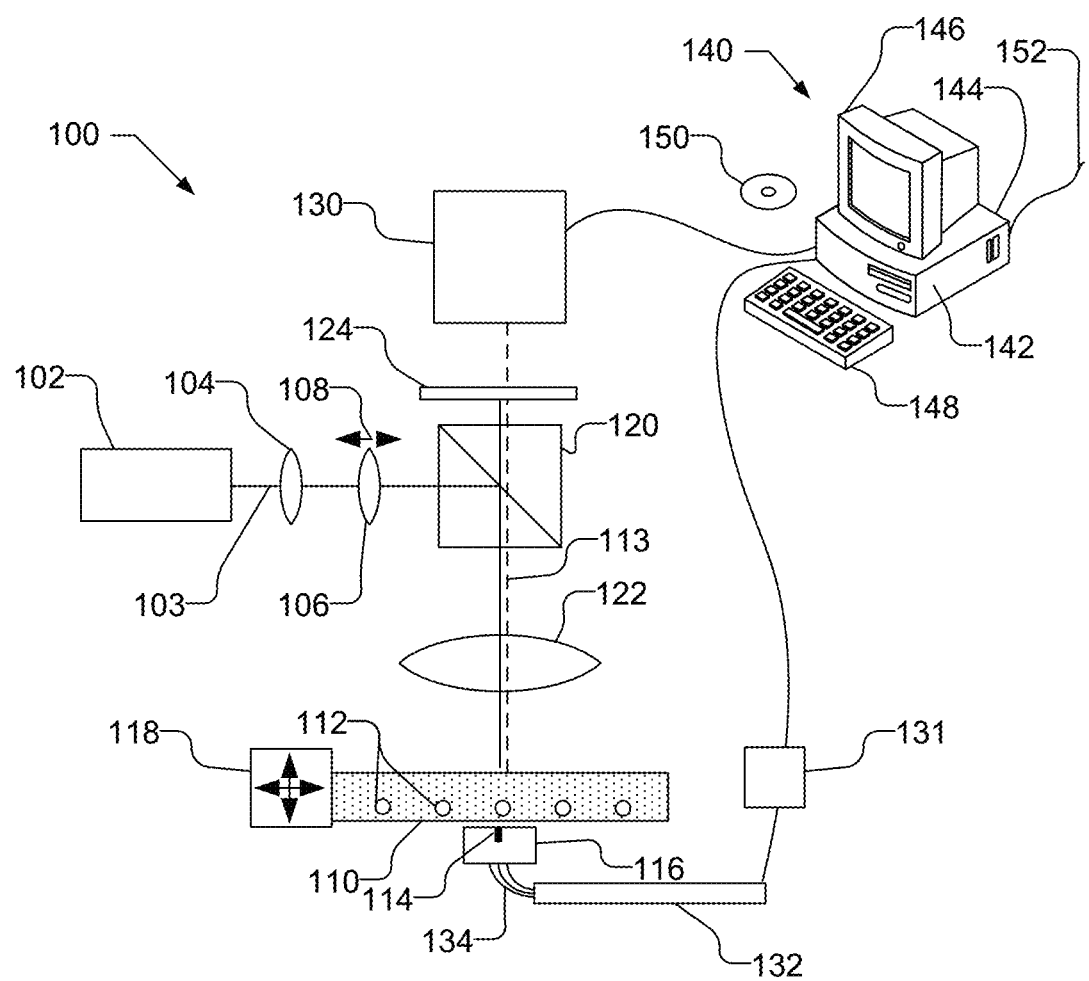
FIG. 1 illustrates an optical metrology device capable of characterizing a photon emitter on a nanometer length scale using photoluminescence produced by a substitutional impurity in a crystal film.

FIG. 1 illustrates an optical metrology device 100 capable of characterizing a photon emitter on a nanometer length scale using photoluminescence (PL) produced by a substitutional impurity 112 in a crystal film 110. For example, one or more nitrogen vacancy centers (NV centers) in a diamond crystal may be used. An NV center is a naturally occurring or technically created impurity in a crystal, such as a diamond crystal where a Nitrogen atom replaces a Carbon atom creating a vacancy next to the Nitrogen atom. The diamond crystal, by way of example, may have a (111) crystal orientation, but other crystalline orientations are possible. If desired, other substitutional impurities in crystals may be used, such as the Silicon-vacancy center in diamond (SAO, but for the sake of simplicity, the present disclosure will refer to nitrogen NV centers in diamond. The crystal film may be, e.g., a crystal that contains a plurality of NV centers or that contains a single (or a few) NV centers. If desired, the film may contain one or a plurality of crystal particles in a suspension forming a film on, e.g. a glass substrate, each crystal particle having one or more NV centers.

The NV centers, which are basically artificial atoms with distinct quantum energy levels, show unique extrinsic and intrinsic optical spin dynamics including stable photoluminescence based on radiating transitions between optically excited energy levels of their charged quantum states. The photoluminescence may be produced by the NV centers in response to excitation illumination. Additionally, the photoluminescence of an NV center may be turned "off" or reduced by the light emitted from a photon emitter that is under test due to a mechanism known as Stimulated Emission Depletion (STED) or alternatively by Ground State Depletion (GSD) or Charge State Depletion (CSD). STED is used in super-resolution (SRM) microscopy to achieve spatial resolution beyond the optical diffraction limit using a laser light source for photoluminescence depletion. Other than in SRM as discussed below, the STED light source in the present disclosure is the device under test. The optical metrology device 100 may optically detect the photoluminescence of one or more NV centers 112 in a crystal film 110, e.g. using photon counting by employing a photo detector on a scanning microscope or by using a camera with high sensitivity. By comparing the detected photoluminescence intensity produced in response to the excitation illumination when no STED illumination from the photon emitter under test is present and the detected photoluminescence intensity produced in response to the excitation illumination in the presence of STED illumination from the photon emitter, the quenching of the photoluminescence intensity may be determined, sometimes referred to herein simply as photoluminescence quenching. The characteristics of the photon emitter, including spatial and power characteristics, may be determined by analyzing the amount of photoluminescence quenching, e.g., by fitting the photoluminescence quenching to a model or comparing the photoluminescence quenching to a library of predetermined data.

The optical metrology device 100 may be, e.g., a microscope such as a confocal microscope or a wide-field microscope. For example, a confocal microscope may include a light source 102 that produces excitation illumination 103 that is incident on the crystal film 110 with the substitutional impurities 112. The use of a confocal detection system enables detection of photoluminescence produced in response to the excitation illumination from only a small volume of the crystal film 110, e.g., 1 $\mu m^3$. The light source 102 may be, e.g., a laser, LED, etc., that excites the NV center with a continuous (CW) or pulsed excitation illumination, with one or more wavelengths in a range of 460 nm to 580 nm, and which may be, e.g., 532 nm. With pulsed excitation illumination, the pulse width may be, e.g., approximately 800 ps with a 4-MHz repetition rate. The light source 102 may have a power density of, e.g., 40 kW/cm$^2$, to polarize the NV center by pumping it between the ground and the excited levels. The light from the light source 102 may be provided to a collimator consisting of lenses 104 and 106 either directly or by way of an intervening optical element, e.g., fiber optics or a light pipe. The collimator 104, 106 expands and collimates the light, which is focused by lens 122, which is also used to collect the photoluminescence emanating from the NV centers. In an embodiment in which the device is a confocal microscope, the lens 106 (and/or other appropriate lens(es)) may be moved back and forth, as illustrated by arrow 108 and/or a 2-dimensional steering-mirror system could be used to move the excitation illumination 103 in the back-aperture plane of the objective lens 122 scanning the focused excitation illumination 103 in the sample plane. Additionally, appropriate apertures may be used in an embodiment in which the microscope is a confocal microscope. Moreover, if desired and as discussed below, additional light sources may be used along with light source 102.

A beam splitter 120 receives the excitation illumination from the light source 102 and provides at least a portion of the excitation illumination to the objective lens 122. The excitation illumination is focused on the surface of the crystal film 110 by the objective lens 122, which may have a high numerical aperture (NA=0.95) or an oil-immersion lens with an NA of, e.g. 1.3. The objective lens 122 may focus the excitation illumination on the crystal film 110 at a normal angle of incidence. It should be understood, however, that an oblique angle of incidence of the excitation illumination may be used if desired. The objective lens 122 focuses the light onto the crystal film 110 with one or more NV centers 112. The crystal film 110 and NV centers 112 are positioned to be in a near field emission of the photon emitter 114 under test. By way of example, FIG. 1 illustrates the photon emitter 114 as a part of a Heat Assisted Magnetic Recording (HAMR) recording head 116. The photon emitter 114, for example, may be a thermal device that heats the recording medium using a laser light source and near-field aperture or a near field transducer. It should be understood, however, that the photon emitter 114 under test may be any other type of device that produces a near field of illumination. In addition to near field emitters, the optical metrology device may be used for characterization of far field photon emitters with nanometer precision, which may be useful for characterizing a laser, e.g., the beam waist of a focused laser, or optical fibers. For example, a focal spot of a focused laser beam may be as small as 200 nm in diameter, which cannot easily be characterized by conventional methods. By scanning the focal spot from a focused laser beam over the NV centers 112 or an optical fiber on the crystal film 110, for example, the profile of the laser beam or optical fiber may be resolved with nanometer resolution.

Figure 2A:
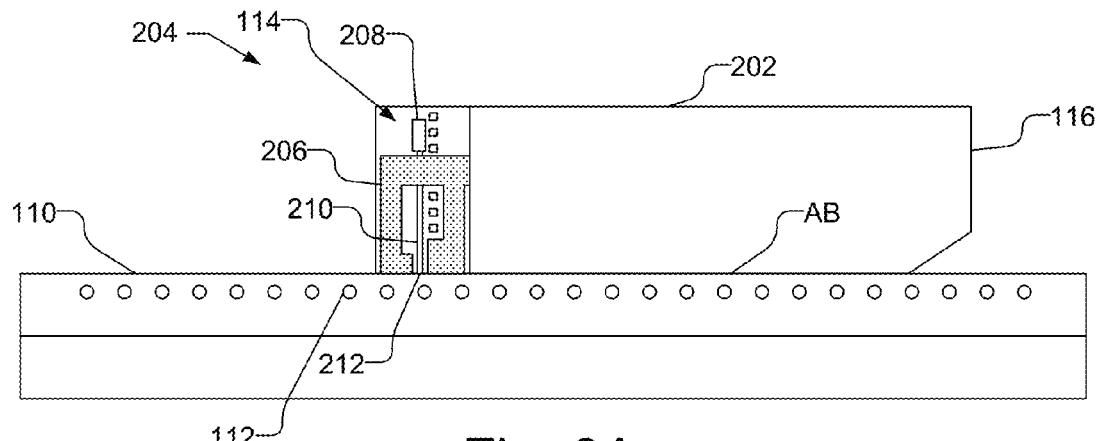
FIGS. 2A and 2B illustrate a side view and a back view, respectively, of a recording head with a photon emitter in contact with crystal film.
Figure 2B:
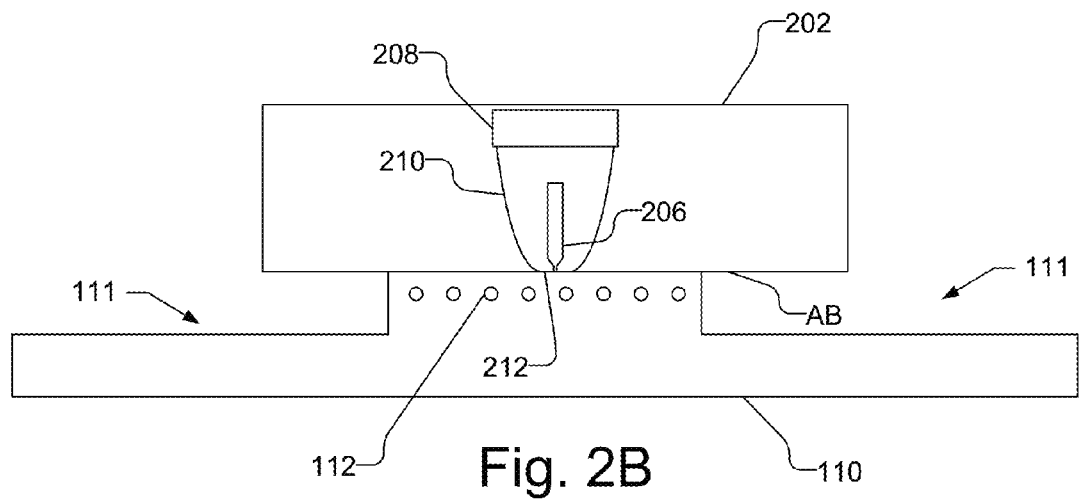

The crystal film 110 may be placed near or in contact with the photon emitter 114, or if desired, deposited on the air bearing surface (ABS) of the recording head 116, e.g., if the photon emitter 114 is part of the recording head. FIGS. 2A and 2B, by way of example, illustrate a side view and a back view, respectively, of recording head 116 in contact with crystal film 110. As illustrated in FIG. 2A, the recording head 116 includes a body, referred to as a slider 202, with a write pole structure 204, illustrated greatly enlarged, coupled to the back end of the slider 202. A light source 208, e.g. a laser diode, that is near the write pole structure 204 including the write pole 206 is integrated into the recording head 116. Light from the integrated light source 208 is coupled to a near field aperture 212 at the ABS via an optical wave guide 210. The near field illumination is produced by the near field aperture 212 at the air bearing surface AB. As can be seen in FIG. 2B, the top surface of the crystal film 110 may be patterned, illustrated with notches 111, forming islands with a width that is greater than a maximum dimension of the expected quenching profile, i.e., the area subject to photoluminescence quenching by STED near field illumination produced by the photon emitter 114. For example, the island width may be approximately half the width of the slider 202 or less. The length of the island is optional and may be greater than the length of the slider 202, and, in fact, may extend the length of the crystal film 110 if desired. The ABS of the recording head 116, and more particularly, the near field aperture 212, may be placed in contact with the crystal film 110 on a patterned island of the crystal film 110.

The NV centers 112 in the crystal film 110 may be arranged in the form of a matrix and may have a uniform or a random distribution with a defined average density. Different average densities of the NV centers 112 in the crystal film 110 may be used depending on how the optical metrology device 100 collects the photoluminescence. By way of example, however, an average density of the NV centers 112 may be, e.g. 200 NV centers per $\mu m^2$ or such that the distance between adjacent NV centers 112 is similar to or less than the dimension of the expected quenching profile, i.e., the area subject to photoluminescence quenching. Alternatively, the crystal film 110 may, in fact, include a number of small crystals, each containing a number of NV centers 112. If desired, optical metrology device 100 may include additional optic elements to move the excitation illumination over the crystal film 110, e.g., in one or two dimensions. In one embodiment, as discussed below, a second light source may be provided that produces STED illumination with a ring shaped beam that has a central zero intensity at the focal plane that is coincident with the excitation illumination and which is scanned over the crystal film 110. Alternatively, a single (or few) NV center 112 may be used in the crystal film 110. In such an embodiment, relative movement between the recording head 116 and the crystal film 110 may be produced, e.g., as illustrated by actuator 118 in FIG. 1.

During measurement, photoluminescence 113 produced by the NV centers 112, illustrated by the dotted line, will be collected by the objective lens 122 and directed by the beam splitter 120 towards a detector 130. As illustrated, a spectral filter 124, such as a dichroic film, is positioned before the detector 130 to remove any reflected excitation illumination and STED illumination from the photon emitter 114 and to direct only the photoluminescence to the detector 130. The spectral filter 124, thus, may be a long-pass filter with a wavelength cut-off at, e.g., 580 nm, or a narrow band pass filter with a center wave length of e.g. 637 nm, to filter out any remaining excitation illumination and STED illumination. The detector 130 may be, e.g., a non-imaging photodetector, such as a silicon avalanche photodiode operating in the signal photon counting regime, which detects the optical intensity at a single spot. Alternatively a CCD camera can be used to detect the intensity of the photoluminescence.

The detector 130 is connected to a computer 140 and the computer 140 receives, stores, and analyzes the optically detected data provided by the detector 130. The computer 140 includes a processor 142 with memory 144, as well as a user interface including e.g., a display 146 and input devices 148. A non-transitory computer-usable storage medium 150 having computer-readable program code embodied may be used by the computer 140 for causing the processor 142 to control the optical metrology device 100 and to perform the functions including the analysis described herein. The data structures and software code for automatically implementing one or more acts described in this detailed description can be implemented by one of ordinary skill in the art in light of the present disclosure and stored, e.g., on a computer readable storage medium 150, which may be any device or medium that can store code and/or data for use by a computer system such as processor 142. The computer-usable storage medium 150 may be, but is not limited to, magnetic and optical storage devices such as disk drives, magnetic tape, compact discs, and DVDs (digital versatile discs or digital video discs). A communication port 152 may also be used to receive instructions that are used to program the computer 140 to perform any one or more of the functions described herein and may represent any type of communication connection, such as to the internet or any other computer network. Additionally, the functions described herein may be stored in memory 144 or embodied in whole or in part within the circuitry of an application specific integrated circuit (ASIC) or a programmable logic device (PLD), and the functions may be embodied in a computer understandable descriptor language which may be used to create an ASIC or PLD that operates as herein described.

As illustrated, the computer 140 may be coupled to the recording head 116, via a probe card 132 which is connected to the recording head 116 using one or more probes 134, which may be, e.g., pogopins, probes, or other contacts such as wires that are wire bonded. The probe card 132 may be coupled to a biasing source 131 that provides a bias signal, such as a current or voltage signal, which is provided to the recording head 116 via the probe card 132 and controls the photon emitter 114, i.e., a high intensity light source, on the recording head 116. If the light source is separate from the recording head 116, e.g., the probe card 132 may control the light source, which is remote from the recording head 116, to produce illumination that is incident on the photon emitter 114, which operates as a near field transducer.

The biasing source 131 may be connected to and controlled by the computer 140. The computer 140, thus, may control the illumination produced by the photon emitter 114 on the recording head 116, e.g., by controlling the bias signal provided to the recording head (or separate illumination source). The biasing source 131 may provide a plurality of bias signals with different levels to the recording head 116. Accordingly, the recording head 116 may be controlled via the biasing source 131 to produce near field illumination with a desired intensity that is constant or varying with a desired pulse width and frequency. The varying near field illumination produced by the photon emitter 114 may vary continuously or in a stepped manner.

Accordingly, the recording head 116 may be controlled via the biasing source 131 to produce a constant or varying near field illumination. Additionally, when the recording head 116 includes a Dynamic-Flying Height (DFH) device, one of the probes 134 of the probe card 132 may be used to provide current to the microactuator device from a second circuit in the current or voltage source that is connected to the computer 140. Write heads use a DFH device as an adjustment mechanism to internally bias the write pole structure, including the photon emitter, closer to or further from the air bearing surface. The DFH device is typically in the form of a heater incorporated into the write head structure, with additional contact pads for external connection. By applying a bias to the additional contact pads via the probe card 132, the position of the photon emitter 114 can be adjusted towards or away from the air bearing surface of the write head. By adjusting the position of the photon emitter 114 via the DFH device, the performance of the photon emitter 114 may be measured at different vertical displacement from the crystal film 110.

Additionally, when the recording head 116 includes a microactuator device, one of the probes 134 of the probe card 132 may be used to provide current to the microactuator device. The source of the current may be a second circuit in the current or voltage source connected to the computer 140. Write heads use a microactuator device as an adjustment mechanism to move the write pole structure, including the photon emitter, in the cross-track direction to better align the write pole structure to the lands of a disk that is being written to. The microactuator device is incorporated into the write head structure, which includes additional contact pads for external connection. By applying a bias to the additional contact pads via the probe card 132, the position of the photon emitter 114 can be adjusted in the cross-track direction. By adjusting the position of the photon emitter 114 via the microactuator device during measurement with the device, the performance of the microactuator may be verified and the characteristics of the photon emitter 114 may be measured at different positions. Additionally, with an adequate density of NV centers, e.g., a low NV center density, and sufficient movement caused by the microactuator device, the microactuator device may be used to produce relative movement between the crystal film 110 and the photon emitter 114 during measurement.

As discussed above, the crystal film 110 contains one or more substitutional impurities 112, such as NV centers. An NV center in diamond is a naturally occurring or technically created impurity in, e.g., a diamond crystal where a Nitrogen atom replaces a Carbon atom creating a vacancy next to the Nitrogen atom. Nitrogen vacancy centers may be created in a diamond crystal, e.g., using a type-Ib HPHT single-crystal sample that is initially embedded with nitrogen impurities. For example, nitrogen impurities may be embedded by irradiation with a an ion-beam, e.g. $N_2^+$ ions at 5 keV, in case of a very high purity diamond film or by an electron beam in case the diamond film already has nitrogen impurities and annealing, e.g., for 2 hours at 850° C. The density of the NV centers within the crystal film may be controlled, e.g., by controlling the applied irradiation dose, or using appropriate masking techniques. For example, an ion beam fluence of $10^{11}$ $cm^2$ can result in a density of $8 \times 10^{10}$ NV $cm^{-2}$. Moreover, by controlling the energy of the implantation as well as the annealing process the depth of the NV centers implanted in the crystal may be controlled.

An NV center may be optically excited, e.g., with excitation illumination having a wavelength range from 460 nm to 580 nm, which yields an intense photoluminescence emission from the NV center with lifetimes in the millisecond range. For example, the NV center may be excited with a laser at a wavelength of 532 nm and in response will emit a broadband luminescence with a zero phonon line at 637 nm, at room temperature. In the mechanism of stimulated emission, an electron in an excited state gives energy to an incoming photon and is forced to the ground state before it can create photoluminescence by spontaneous emission.

In addition, the photoluminescence of an NV center may be turned "off" or the intensity reduced in time when the pulse of excitation illumination is followed by a longer wavelength, or with the same wavelength, pulse of sufficient intensity, e.g., from the photon emitter 114 under test, due to a mechanism known as Stimulated Emission Depletion (STED). By way of example, the excitation illumination may have a wavelength of 532 nm and a duration of 60 ps followed by a longer wavelength pulse from the photon emitter 114 under test, e.g. 830 nm, with a duration 3.2 ns, of sufficient intensity to quench the intensity of the photoluminescence. If desired, STED with a continuous (CW) or quasi CW illumination may be employed.

Additionally, STED illumination may be used by the optical metrology device 100 itself to improve spatial resolution by functionally switching off the photoluminescence from a portion of NV centers, e.g., STED microscopy. For example, STED microscopy can be implemented by combining the excitation been with STED illumination that has a focal intensity distribution ISTED featuring a central zero intensity, such as a disk shape. The STED illumination is coincident with the excitation illumination on the crystal film. Overlapping the Airy disk (Point Spread Function) of the excitation illumination having an intensity $I_S$ with the ring shaped STED illumination and enforcing ISTED>>$I_S$ switches off the NV centers covered by the Airy disk (diffraction limited) of the excitation illumination except for those NV centers at the STED illumination minimum where ISTED<$I_S$. Thus, the Airy disk of the excitation illumination may be ignored when calculating the spot size in which NV centers may still be "on," i.e., responsive to the excitation illumination, and therefore, the effective point-spread function (PSF) of the system is no longer diffraction limited. Although the resolution Dx,y scales with the wavelength, adjusting $I_{max}$, the STED illumination maximum, squeezes the STED SPSF (Stimulated Point Spread Function) continuously, and therefore wavelength is not a limiting factor. An advantageous property of the use of STED illumination is that when scanned over the crystal film together with the excitation illumination, the ring-shaped STED light intensity enables a reduced number of NV centers, e.g., a single NV center, to fall within the ring minimum. The stimulated point spread function determines the effective photoluminescence detection resolution, i.e., it is a characteristic of the apparatus and determines the minimum distance between two NV centers where the two NV centers can still be discriminated. All other NV centers are switched "off" by the STED illumination or simply not excited by the excitation illumination. Thus, with the use of a STED illumination, NV centers may be resolved individually, thereby further improving the spatial resolution of measurements, and may obviate the need to physically produce relative movement between the crystal with NV centers and the photon emitter to produce a two dimensional scan of the photon emitter.

Additionally, if desired, Ground State Depletion (GSD) may be used, as opposed to STED, to improve spatial resolution of the metrology device 100. Similar to STED, GSD uses quenching illumination to functionally switch off a portion of NV centers, but unlike STED, GSD uses the same wavelength for the excitation illumination and the quenching illumination.

Thus, one or more NV centers in a crystal film may be used to measure characteristics of the photon emitter, including spatial and power characteristics by detecting quenching of the photoluminescence intensity produced by NV centers caused by the near field illumination of the photon emitter. The photoluminescence quenching data may be analyzed, e.g., by fitting to a model or comparing a library of data, to determine the desired characteristics of the photon emitter.

Figure 3:
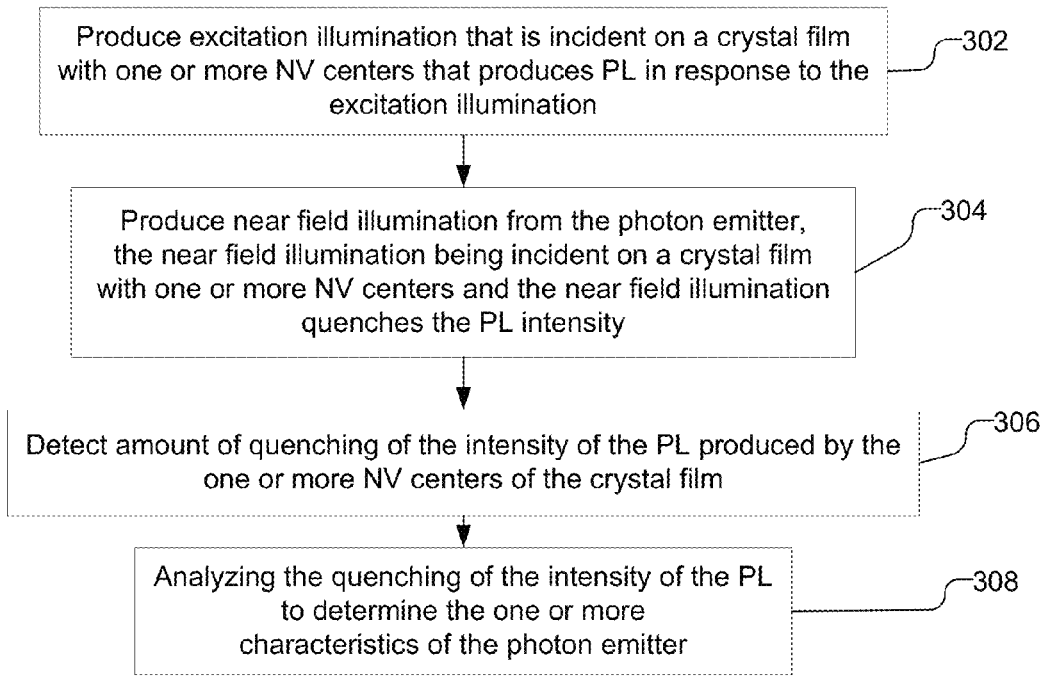
FIG. 3 is a flow chart illustrating a method of determining one or more characteristics of a photon emitter using nitrogen vacancy centers in a crystal film and an optical metrology device.

FIG. 3, by way of example, is a flow chart illustrating a method of determining one or more characteristics of a photon emitter using NV centers and an optical metrology device, such as the optical metrology device 100. As illustrated, excitation illumination is produced, e.g., by the optical metrology device 100, and is incident on a crystal film with the one or more NV centers (302). As discussed above, the NV centers produce photoluminescence having an intensity in response to the excitation illumination. Illumination is produced from the photon emitter, where the illumination is incident on the crystal film with the one or more NV centers (304). The illumination produced by the photon emitter quenches the intensity of the photoluminescence from the one or more nitrogen vacancy centers. The illumination from the photon emitter may be near field illumination or far field illumination. For example, the illumination may be produced by providing a bias signal to the photon emitter, which causes the photon emitter to generate near field illumination. Where the photon emitter is a laser diode, a bias current may be used, but a bias voltage may be used for other types of light sources if appropriate. For example, if the photon emitter may include a laser light source and near field aperture on a recording head, the bias current may be provided to the recording head via the probe card 132 to cause the photon emitter to emit the near field illumination. Alternatively, the light source may be remote from the photon emitter, e.g., as illustrated with the near field transducer 114 in FIG. 2A, where light from the remote light source is provided to the near field transducer, which produces the near field illumination in response. The illumination may be far field illumination, such as that produced by a laser or fiber optics.

The amount of quenching of the intensity of the photoluminescence produced by the one or more NV centers caused by the illumination of the photon emitter is detected (306). The amount of quenching of the intensity of the photoluminescence may be detected by subtracting the background photoluminescence intensity. In other words, a first photoluminescence intensity may be detected from the one or more NV centers in response to the excitation illumination without the presence of the illumination produced by the photon emitter. A second photoluminescence intensity may be detected from the one or more NV centers in response to the excitation illumination in the presence of the illumination produced by the photon emitter, i.e., while the illumination from the photon emitter quenches the intensity of the photoluminescence from the NV centers. The amount of quenching of the intensity of the photoluminescence may then be determined based on a difference between the first photoluminescence intensity and the second photoluminescence intensity.

The amount of quenching of the intensity of the photoluminescence is analyzed to determine the one or more characteristics of the photon emitter (308). For example, the amount of quenching of the intensity of the photoluminescence may be analyzed by fitting the detected amount of quenching of the intensity of the photoluminescence to a photoluminescence quenching model. By way of example, the detected amount of photoluminescence quenching may be used in a non-linear, multi parameter fit to a model of a photoluminescence quenching distribution profile to determine the desired characteristics of the photon emitter. Additionally, or alternative, the amount of quenching of the intensity of the photoluminescence may be analyzed by comparing the amount of quenching of the intensity of the photoluminescence to a library of data, which is pre-generated and stored, e.g., in memory of the metrology device. The pre-generated data in the library may be produced, e.g., using the photoluminescence quenching model or in any other desired manner, such as empirically. The amount of quenching of the intensity of the photoluminescence may be analyzed in other manners as will be evident to those of ordinary skill in the art in light of the present disclosure. Characteristics that may be determined by analyzing the amount of quenching of the intensity of the photoluminescence, for example, may be the peak power or a width of the distribution profile. The width of the profile, for example when using a Lorentzian, may be the Full Width Half Magnitude (FWHM) or FWHM Half Magnitude (HWHM) or other equivalent measure, but for the sake of ease of reference will be referred to herein as FWHM. The characteristics of the photon emitter may be determined for different bias currents provided to the photon emitter. Moreover, the quenching data may be detected as a function of the bias current provided to the photon emitter and analyzed, e.g., by fitting to a photoluminescence quenching model of an integrated photoluminescence quenching profile or comparing to a library of data to determine characteristics such as the width of the distribution profile and a power scaling factor. Again, the library of data may be produced, e.g., using the photoluminescence quenching model of an integrated photoluminescence quenching profile or in any other desired manner, such as empirically.

Figure 4:
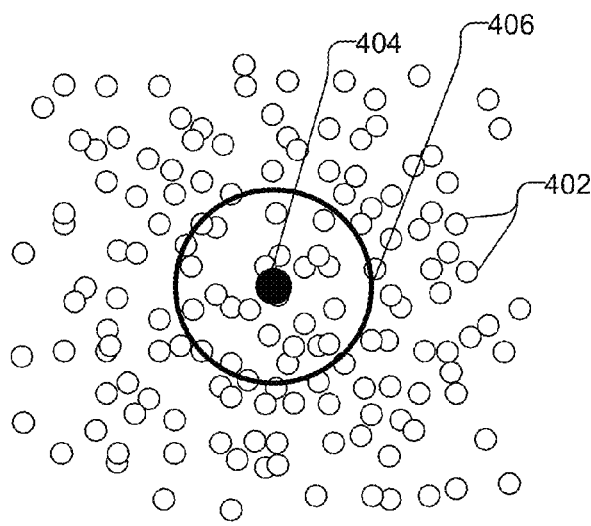
FIG. 4 shows a portion of a crystal film with a plurality of luminescing nitrogen vacancy centers and a photon emitter.

FIG. 4, by way of illustration, shows a portion of a crystal film with a plurality of luminescing NV centers 402, illustrated as white spots, only a couple of which are labeled 402. As can be seen, the distribution of NV centers 402 may be inhomogeneous, i.e., non-uniform, but a crystal film with a homogeneous, i.e., uniform, distribution of NV centers may be used if desired. The crystal film, by way of example, may be a single crystal with a number of NV centers or a plurality of nano-crystals combined into the film, each nano-crystal containing one or more NV centers. The NV centers are in the same x/y plane and may have a defined average density, e.g., of 200 NV centers per square micron, or an average spacing of 60 nm±30 nm, but other average densities and/or average spacing may be used depending on the physical characteristics of the photon emitter under test. The spatial resolution is determined by the distance between the near-field illumination and the NV centers. Accordingly, for nanometer scale resolution, the NV centers should be relatively close to the top surface of the crystal film, e.g., a distance of 5 nm or less.

As discussed above, the NV centers are excited with excitation illumination at a wavelength of 532 nm, and luminesce at 637 nm, which may be collected, e.g., using a wide-field microscope with a CCD camera or a scanning microscope with a photodetector. The illumination from the photon emitter, however, will quench, i.e., turn off or reduce the intensity photoluminescence of the NV centers, due to STED. FIG. 4 illustrates a photon emitter 404 under test as a spot and further illustrates a diffraction limited spot 406 of the imaging system as a reference. By way of example, the photon emitter 404 may have a wavelength of, e.g., 700 nm to 900 nm and may be a continuous wave (CW) or pulsed light emitter.

Figure 5:
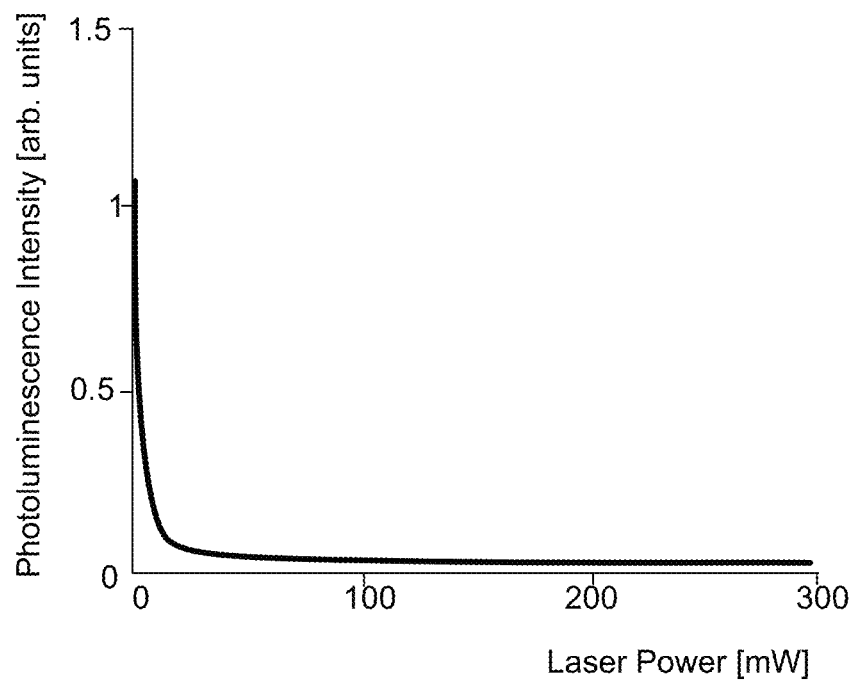
FIG. 5 is a graph illustrating the quenching of the photoluminescence intensity produced by nitrogen vacancy centers caused by a near-infrared continuous wave laser beam.

The crystal film with NV centers has a characteristic dependence of STED on the power of the quenching light source. FIG. 5, by way of example, illustrates the quenching of the photoluminescence intensity produced by the NV centers, i.e., the background subtracted photoluminescence intensity, caused by a near-infrared CW laser beam, where the y-axis represents photoluminescence intensity in arbitrary units, and the x-axis represents the laser power of the quenching light source in mW. The photoluminescence quenching dependence DP is described by an exponential function as follows:

$$DP(I) = m(I-I_0)^n + \text{const} \qquad \text{eq. 1}$$

where "I" represents the general intensity, which may be uniform or locally varying, of the quenching light source, m is the quenching scaling factor and n the quenching exponent, and const is the asymptotic depletion value for very high depletion light intensity, for example, at 300 mW illustrated in FIG. 5. The power dependence of the crystal film has to be measured once to determine the parameters $I_0$, m, n and const. The calibration of the power dependence of the crystal film may be performed using an external laser light source, e.g., laser, with known intensity I to produce data such as that shown in FIG. 5. Preferably, the calibration of the power dependence of the crystal film is performed at the location on the crystal film that will be used to test photon emitters, but if the average density of NV centers is uniform over the entire crystal film, calibration of the power dependence of the crystal film may be performed anywhere on the crystal film.

Figure 6:
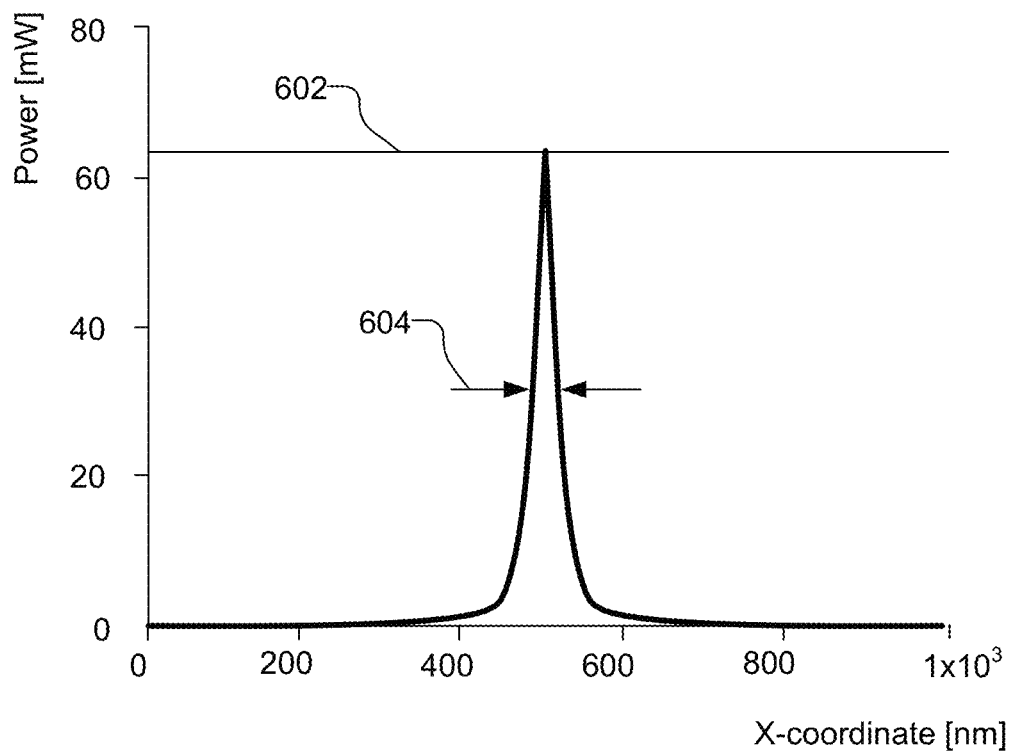
FIG. 6 is a graph illustrating a near field illumination profile for a near field photon emitter.

The photon emitter may be characterized based on its peak power and its spatial distribution. FIG. 6, by way of example, illustrates a near field illumination profile for a near field photon emitter, where the y-axis represents power of the photon emitter in mW and the x-axis represents the x-coordinate in nm. The peak power of the near field illumination profile is illustrated by line 602 and the FWHM is illustrated by arrows 604. The near field illumination profile NF is described by a Lorentzian function with a parameter w that is the FWHM of the near-field distribution determined by the aperture size and the peak power (P) of the photon emitter as follows:

$$NF(x, y, P) = P \frac{w^2}{4[(x-x_0)^2 + (y-y_0)^2] + w^2} \qquad \text{eq. 2}$$

where $x_o$ and $y_0$ are the coordinates with the peak power P. A Lorentzian function is used in a model as an example but this could also be a Gaussian or any other function that can describe the near-field distribution. The use of different model functions may yield different or additional characteristic parameters of the photon source related to the extent and geometry of the near-filed distribution.

Figure 7:
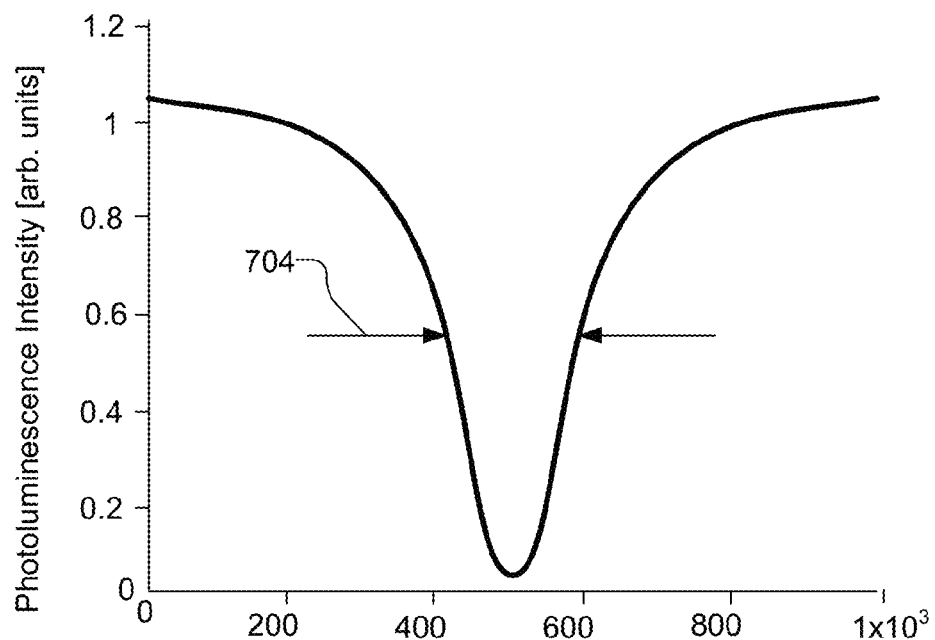
FIG. 7 is a graph illustrating an example of a photoluminescence quenching profile for the nitrogen vacancy centers of a crystal film.

FIG. 7 illustrates an example of a photoluminescence quenching profile for the NV centers of a crystal film, where the y-axis represents photoluminescence intensity in arbitrary units and the x-axis represents the x-coordinate in nm. As can be seen with a comparison of FIGS. 6 and 7, the FWHM of the photoluminescence quenching profile (illustrated by arrows 704) may be larger than the FWHM of the near field illumination profile. The locally varying photoluminescence quenching $I_{STED}$ may be using equation 2 and equation 1 as follows:

$$I_{STED}(x,y,P) = DP(NF(x,y,P)) \qquad \text{eq. 3}$$

Substituting NF(x,y,P) in equation 2 for the intensity I in equation 1, results in the following:

$$I_{STED}(x, y) = m\left[P\frac{w^2}{4[(x-x_0)^2 + (y-y_0)^2] + w^2} - I_0\right]^n \qquad \text{eq. 4}$$

where $I_{STED}(x, y)$ is the locally varying amount of quenching of the intensity of the photoluminescence with const=0, and P and w are fitting parameters of the peak power and the FWHM of the near field illumination profile, respectively, for a rotationally symmetric distribution.

Figure 8:
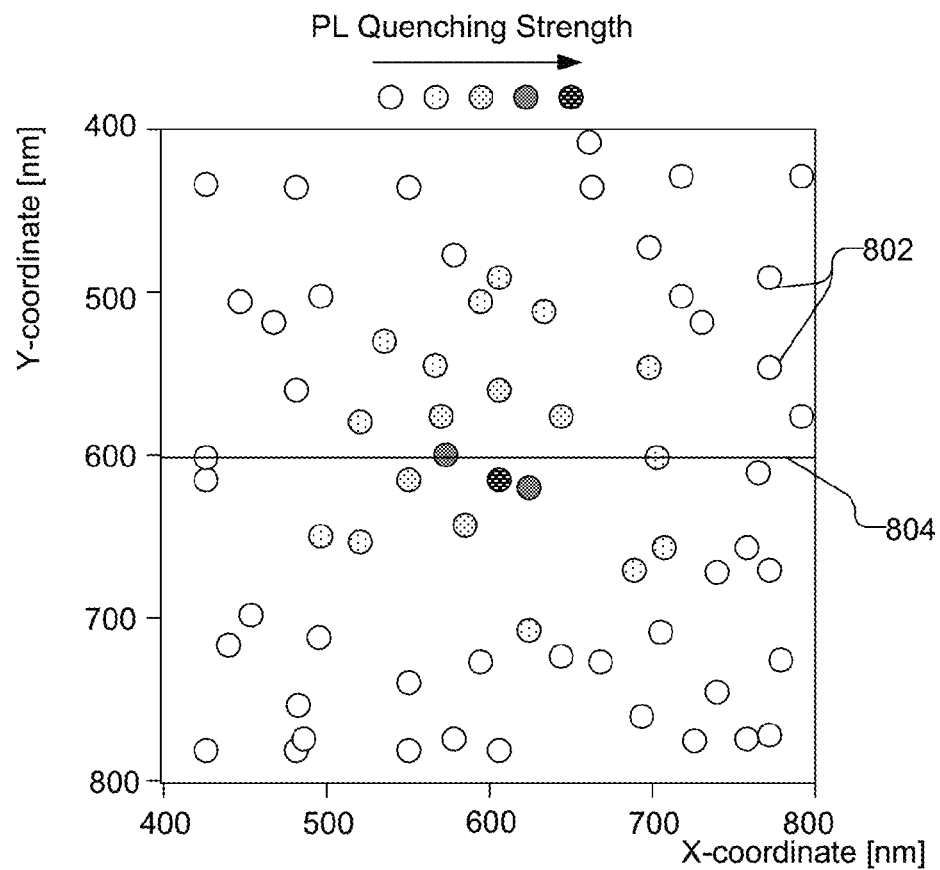
FIG. 8 illustrates detected quenching of the photoluminescence intensity produced by nitrogen vacancy centers, which may be caused by near field illumination of a photon emitter.

FIG. 8, by way of illustration, shows in two dimensions the detected quenching of the intensity of the photoluminescence produced by the NV centers 802 caused by near field illumination of a photon emitter. In FIG. 8, the NV centers are illustrated as spots, with darker spots representing increased quenching. The near field illumination produced by the photon emitter interacts with the NV centers 802 turning off or reducing the intensity of the photoluminescence for individual NV centers when the near field illumination at the individual NV centers is greater than a characteristic threshold value. The photoluminescence quenching of FIG. 8 may be determined as the difference in the measured photoluminescence intensity from the NV centers without the quenching illumination from the photon emitter and the measured photoluminescence intensity from the NV centers in the presence of the quenching illumination from the photon emitter. The intensity of the photoluminescence from the NV centers may be measured using, e.g., a wide-field microscope with a CCD camera or a scanning microscope with a photodetector, which may be scanned in the x and y coordinates. Once the photoluminescence quenching is detected, it may be analyzed, e.g., by fitting to a photoluminescence quenching model or compared to a library of data, to determine the desired characteristics of the photon emitter.

Figure 9:
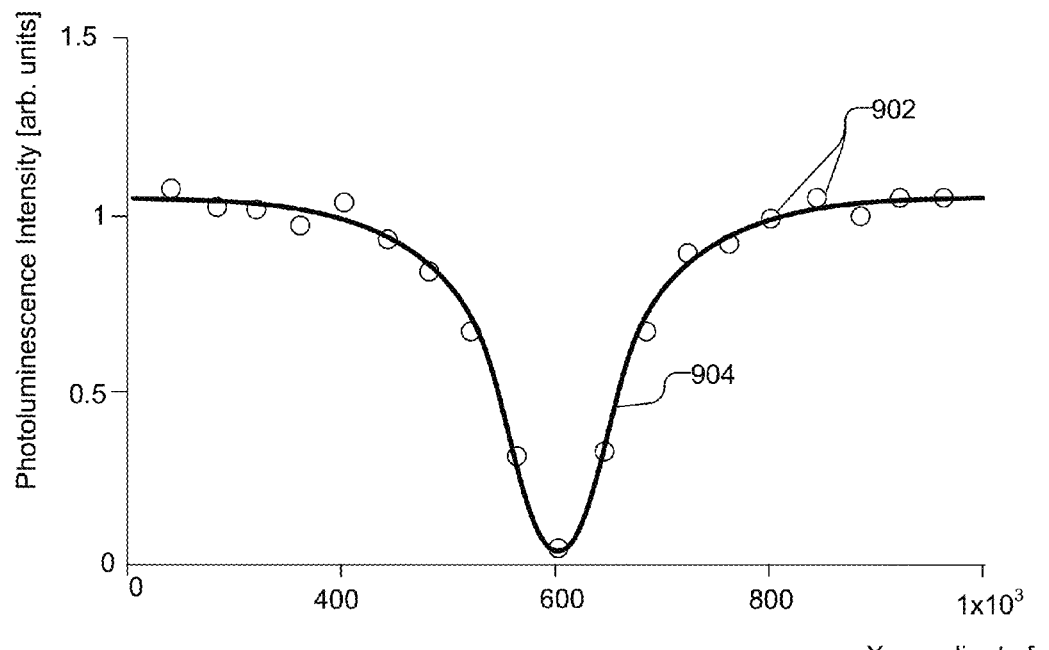
FIG. 9 illustrates detected quenching of the photoluminescence intensity produced by nitrogen vacancy centers along with a fit curve illustrating a spatially resolved photoluminescence quenching profile.

FIG. 9, by way of illustration, shows detected photoluminescence quenching data, i.e., the amount of quenching of the intensity of the photoluminescence from the NV centers, as spots 902, along with a fit curve 904 illustrating a spatially resolved quenching profile. The photoluminescence quenching data may be detected along a horizontal line 804 in FIG. 8. The center line 804 may be determined from a two-dimensional distribution of the photoluminescence quenching data as a line that extends through the point or area with the strongest quenching. The two-dimensional distribution of the photoluminescence quenching data may be produced from a two-dimensional scan of the photon emitter. Alternatively, a one-dimensional scan of the photon emitter may be used to produce the photoluminescence quenching data from the NV centers if the scan passes through the point or area with the strongest quenching. The detected photoluminescence quenching data may be analyzed, e.g., by fitting to a photoluminescence quenching model, such as equation 4, or compared to a library of data, which may be produced using the model or empirically, to determine the one or more characteristics of the photon emitter. Thus, for example, a non-linear, multi parameter fit to the photoluminescence quenching profile model may be used to determine the peak power P and the width of the near field illumination profile. For example, the parameter fit such as that illustrated in FIG. 9 may provide a FWHM of 29.03 nm and a peak power P of 3083 [a.u.] for the near field illumination profile.

Additionally, by varying the separation between the photon emitter and the NV centers, the decay of the near-field power in the z-direction may also be measured. The separation between the photon emitter and the NV centers may be controlled by moving the crystal film, e.g., using a Atomic Force Microscope (AFM) or other actuator holding the crystal film and/or by moving the photon emitter, e.g., using a dynamic fly height (DFH) adjustment on the recording head.

If desired, the photoluminescence quenching may be detected for varying bias currents that are applied to the photon emitter and the peak power and FWHM of the near field illumination profile may be determined for different bias currents.

Figure 10:
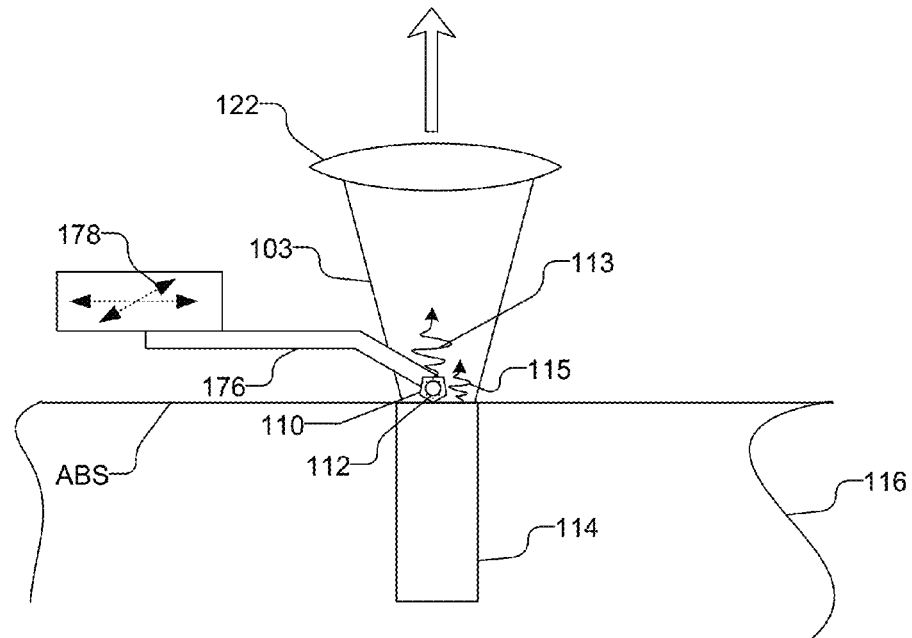
FIG. 10 schematically illustrates a crystal film with one or more nitrogen vacancy centers held on the tip of an Atomic Force Microscope (AFM) cantilever that may be used to detect the photoluminescence quenching caused by a photon emitter on a recording head.

The optical metrology device 100 shown in FIG. 1 may detect the quenching of the intensity of the photoluminescence caused by a near field photon emitter in various manners. For example, FIG. 10 schematically illustrates one implementation in which a crystal film 110 with one or more NV centers 112 is held on the tip of an Atomic Force Microscope (AFM) arm 176 and is in contact with or at a controlled distance from the photon emitter 114 on the recording head 116. The crystal film 110 may be a micron sized diamond particle that includes a single or several NV centers 112. The AFM arm 176 may be scanned over the photon emitter 114 on the recording head 116 in one or two dimensions, as illustrated by arrows 178. As discussed above, a light source 102 (shown in FIG. 1) produces excitation illumination 103 that is focused by the objective lens 122 onto the crystal film 110. In response to the excitation illumination 103, the NV center 112 produces photoluminescence 113 that is collected by the objective lens 122 and provided to the detector 130 (shown in FIG. 1). As the crystal film 110 is scanned across the recording head 116, including the photon emitter 114 and ABS, at each measurement position, the intensity of the photoluminescence 113 is measured with and without the near field illumination 115 from the photon emitter 114 to detect the quenching of the intensity of the photoluminescence at each measuring position. With the photoluminescence quenching detected at a plurality of measuring positions, a one dimensional line profile or two-dimensional distribution of the photoluminescence quenching may be determined. With a two-dimensional distribution of the photoluminescence quenching, the line profile through the strongest quenching point may be used to derive the peak power or the width of the near field illumination profile of the photon emitter by analyzing the amount of quenching of the intensity of the photoluminescence, e.g., by fitting to a photoluminescence quenching model, or compared to a library of data, which may be produced using the model or empirically, as discussed above. If desired, the scan may be repeated for different values of the bias current supplied to the light source, or equivalently, different values of the bias current may be supplied to the light source at each position during a single scan of the crystal film 110.

Figure 11:
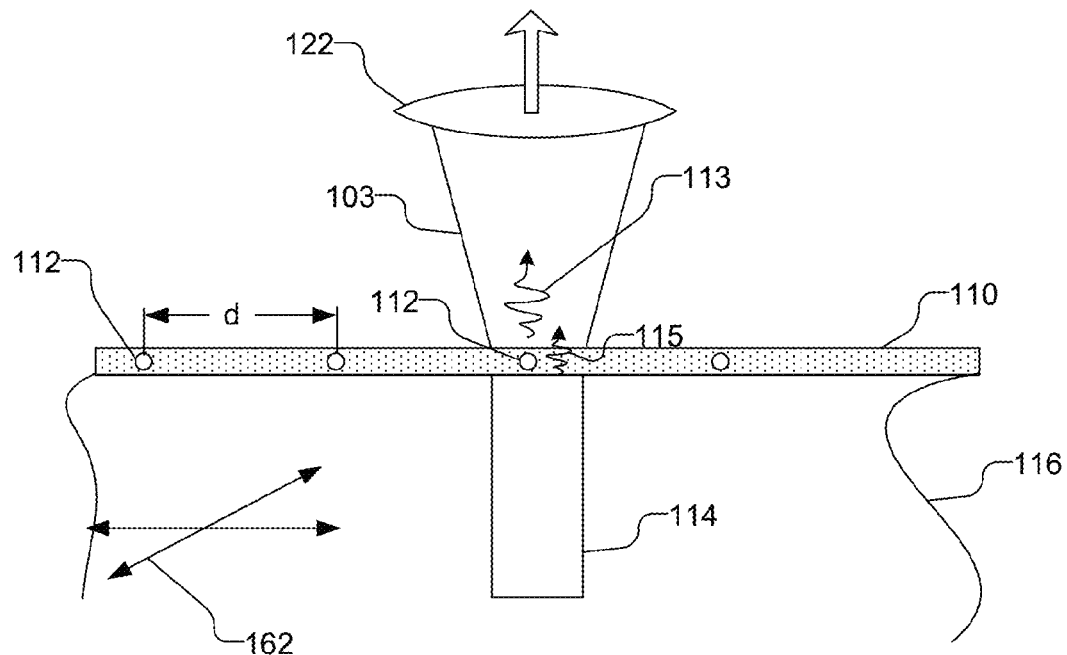
FIG. 11 schematically illustrates a crystal film with a plurality of nitrogen vacancy centers with a relatively low average density, where relative movement between the crystal film and photon emitter may be used to detect the photoluminescence quenching caused by a photon emitter on a recording head.

Another example of how the optical metrology device 100 may detect the quenching of the intensity of the photoluminescence caused a near field photon emitter is shown in FIG. 11. FIG. 11 schematically illustrates a crystal film 110 with a plurality of NV centers 112 that have a relatively low average density, e.g., the average distance d between adjacent nitrogen vacancy centers is equal to or greater than two times a FWHM of the expected quenching profile. The crystal film 110 is positioned so that the near field illumination 115 when produced by the photon emitter 114 will be incident on the crystal film 110. As discussed above, a light source 102 (shown in FIG. 1) produces excitation illumination 103 that is focused by objective lens 122 onto the crystal film 110 with and without the near field illumination 115 of the photon emitter 114. By way of example, the objective lens 122 may produce a narrow focus of the excitation illumination 103 on the surface of the crystal film 110. In response to the excitation illumination 103, the NV center 112 produces photoluminescence that is collected by the objective lens 122 and provided to the detector 130 (shown in FIG. 1). As discussed above in FIGS. 2A and 2B, the surface of the crystal film 110 may be patterned to form protruding islands, e.g., having a diameter that may be slightly larger than the maximum dimension of the expected quenching profile. Relative movement between the photon emitter 114 and the crystal film 110 may be produced in two dimensions, e.g., by moving the recording head 116 with respect to the crystal film 110 or moving the crystal film 110 with respect to the recording head 116, thereby scanning a single NV center over the photon emitter 114 in two dimensions, as illustrated by arrows 162. The crystal film 110 and recording head 116 may be in contact during each measurement, as illustrated in FIG. 11, and separated before moving to the next measurement position. The photoluminescence quenching data is detected at a plurality of positions to determine a two-dimensional distribution of the photoluminescence quenching. A line profile through the strongest quenching point in the two-dimensional distribution of the photoluminescence quenching may be used to derive the peak power and the width of the near field illumination profile of the photon emitter by analyzing the amount of quenching of the intensity of the photoluminescence, e.g., by fitting to a photoluminescence quenching model, or compared to a library of data, which may be produced using the model or empirically, as discussed above. If desired, the scan may be repeated for different values of the bias current supplied to the light source, or equivalently, different values of the bias current may be supplied to the light source at each position during a single scan of the crystal film 110.

Moreover, as discussed above, by varying the separation between the photon emitter and the NV centers, the decay of the near-field power in the z-direction may also be measured. The separation between the photon emitter and the NV centers may be controlled by moving the crystal film, e.g., using an actuator holding the crystal film and/or by moving the photon emitter, e.g., using a dynamic fly height (DFH) adjustment on the recording head. Further, the photoluminescence quenching may be detected for varying bias currents that are applied to the photon emitter and the peak power and width of the near field illumination profile may be determined for different bias currents.

In another implementation, the photoluminescence quenching of the intensity of the photoluminescence produced by a near field photon emitter may be detected without using relative movement between the photon emitter and the crystal film. For example, the optical metrology device may use scanning external STED illumination while the photon emitter and crystal film are held stationary with respect to each other.

FIG. 12 illustrates, by way of example, the optical metrology device 100 with additional light sources to produce STED illumination to improve resolution and to scan the photon emitter. As illustrated, optical metrology device 100 includes a second light source $102_{STED}$ that produces STED illumination $103_{STED}$ having a different wavelength as the light source 102, and that is coincident on the crystal film 110 with the excitation illumination 103 from light source 102. The light source 102 produces excitation illumination 103 that has a Gaussian point spread function and produces a relatively large diffraction limited spot on the crystal film 110. FIG. 13, by way of example, illustrates the Gaussian point spread function of the excitation illumination 103 with a solid line. The second light source $102_{STED}$ produces light that passes through a vortex phase plate 164 to produce a ring shaped beam that has a central zero intensity at the focal plane. FIG. 13, by way of example, illustrates a ring shaped point intensity distribution of the STED illumination $103_{STED}$, which is coincident with the excitation illumination 103. The STED illumination $103_{STED}$ quenches the intensity of the photoluminescence produced by the NV centers 112 in the crystal film 110 that are off-center relative to the excitation illumination 103, so that the off-center NV centers only contribute a constant background, which may be subtracted from the photoluminescence quenching signal produced by the photon emitter 114 under test, thereby providing a photoluminescence quenching signal from only the NV centers in the center of the STED illumination $103_{STED}$. FIG. 14 illustrates the effective point intensity distribution 166 of the excitation illumination 103 combined with the STED illumination $103_{STED}$. The coincident excitation illumination 103 and STED illumination $103_{STED}$ may be scanned over the crystal film 110 at the region of interest by two-dimensional deflection in the back aperture of the objective lens 122 to detect the photoluminescence quenching caused by the photon emitter 114 in two dimensions, e.g., using one or more mirrors 117 in the beam path, which may be controlled by the computer 140.

The STED illumination $103_{STED}$ may have a wavelength greater than the excitation illumination 103, e.g., greater than 532 nm, and with increased power. For example, a reduction in the photoluminescence may be achieved for STED illumination $103_{STED}$ with power greater than 2 MW/cm$^2$. The STED illumination $103_{STED}$ may be continuous (CW) or pulsed excitation, with a pulse width of, e.g. 150 ps, where a pulsed STED illumination $103_{STED}$ results in stronger quenching of the intensity of the photoluminescence.

Figure 15:
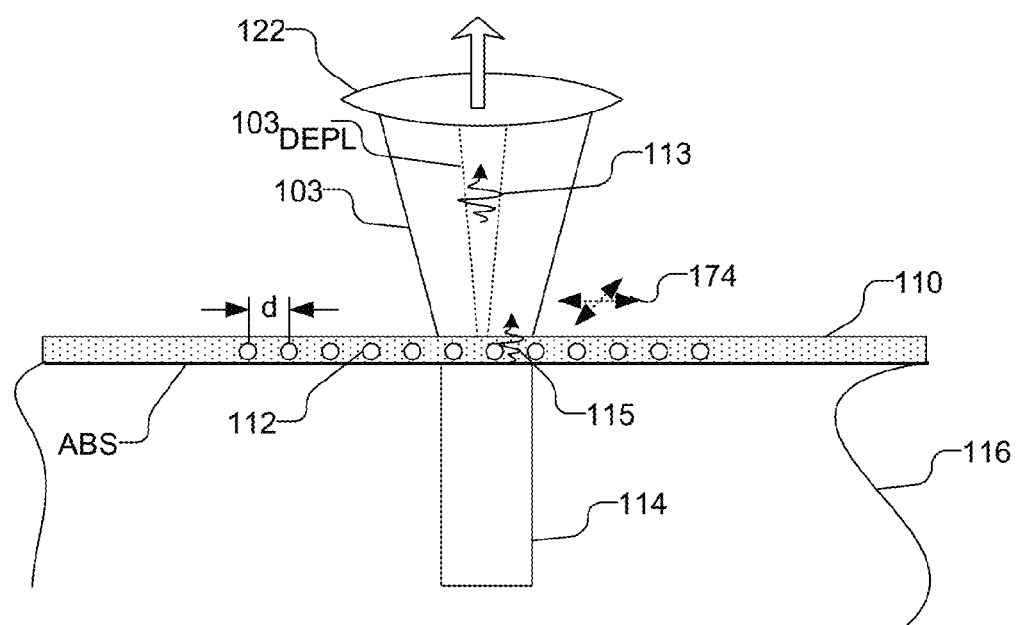
FIG. 15 schematically illustrates a crystal film with a plurality of nitrogen vacancy centers with a relatively high average density and using a combined excitation illumination and external STED illumination to detect the photoluminescence quenching caused by a photon emitter on a recording head.

FIG. 15 schematically illustrates the detection of the quenching of the intensity of the photoluminescence quenching caused by a near field photon emitter using a combined excitation illumination 103 and external STED illumination $103_{STED}$. As illustrated in FIG. 15, the NV centers 112 in the crystal film 110 have a relatively high average density, e.g., the average distance d between adjacent nitrogen vacancy centers is less than two times a FWHM of an expected quenching profile. The density of NV centers may be chosen so that a plurality of NV centers, e.g. 10×10 NV centers, is located under the expected quenching area. The crystal film 110 may be placed in contact with the photon emitter 114, e.g., by being placed in contact with the ABS of the recording head 116. As discussed above in FIGS. 2A and 2B, the surface of the crystal film 110 may be patterned to form protruding islands, e.g., having a diameter that may be slightly larger than the maximum dimension of the expected quenching profile. The coincident excitation illumination 103 and external STED illumination $103_{STED}$ enables a reduced number of NV centers to be resolved, e.g., only NV centers that fall within the ring minimum of the external STED illumination $103_{STED}$ are resolved. Thus, the quenching effect of the near field illumination 115 of the photon emitter 114 may be detected at only the NV centers that fall within the ring minimum of the external STED illumination 103 STED. The coincident excitation illumination 103 and STED illumination $103_{STED}$ may be scanned in two dimensions over the region of interest, as illustrated by arrows 174, e.g., using an arrangement of mirrors in the beam path, thereby obviating the needs for an actuator to produce relative movement between the recording head and the crystal film 110. The photoluminescence quenching data is detected at a plurality of positions during the scan of the coincident excitation illumination 103 and STED illumination $103_{STED}$ to determine a two-dimensional distribution of the photoluminescence quenching data. A line profile through the strongest quenching point in the two-dimensional distribution of the photoluminescence quenching data may be used to derive the peak power and the width of the near field illumination profile of the photon emitter by analyzing the amount of quenching of the intensity of the photoluminescence, e.g., by fitting to a photoluminescence quenching model, or compared to a library of data, which may be produced using the model or empirically, as discussed above. If desired, the scan may be repeated for different values of the bias current supplied to the light source, or equivalently, different values of the bias current may be supplied to the light source at each position during a single scan of the crystal film 110.

Moreover, as discussed above, by varying the separation between the photon emitter and the NV centers, the decay of the near-field power in the z-direction may also be measured. The separation between the photon emitter and the NV centers may be controlled by moving the crystal film, e.g., using an actuator holding the crystal film and/or by moving the photon emitter, e.g., using a dynamic fly height (DFH) adjustment on the recording head. Further, the photoluminescence quenching may be detected for varying bias currents that are applied to the photon emitter and the peak power and width of the near field illumination profile may be determined for different bias currents.

Figure 16:
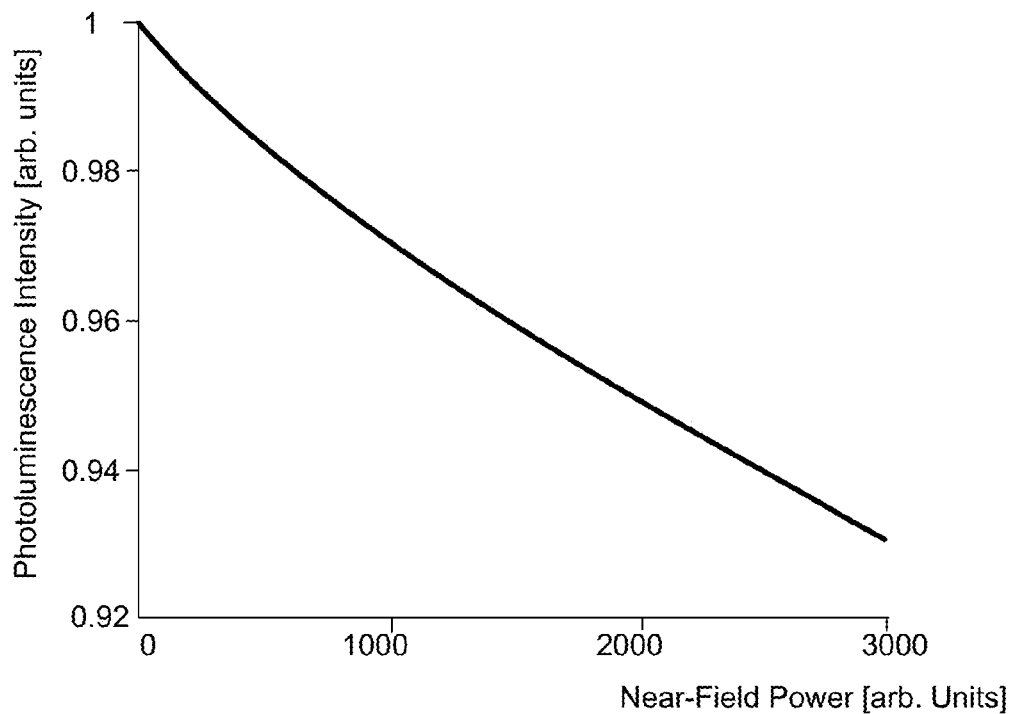
FIG. 16 is a graph illustrating the integrated photoluminescence intensity with respect to the near-field power.

In another implementation, the quenching of the intensity of the photoluminescence caused by a near field photon emitter may be detected without using relative movement between the photon emitter and the crystal film by detecting integrated photoluminescence as a function of bias current. The integrated photoluminescence may be detected, e.g., using wide-field excitation illumination that is incident on a crystal film 110 with relatively high average density and collecting the resulting photoluminescence from an area that is larger than the maximum expected quenching area. Wide field illumination, as used herein, refers to illumination used with microscopy having a homogeneously illuminated field of view to form an image, as compared to scanning a focused beam. FIG. 16, by way of example, illustrates the integrated photoluminescence intensity $Int_{STED}$ in arbitrary units with respect to the near-field power in arbitrary units. The integrated photoluminescence intensity $Int_{STED}$, as a sum over all NV centers contributing to the emitted photoluminescence, may be written as:

$$Int_{STED}(P, w) = \sum_{NV} I_{STED}(NV, w, P) \qquad \text{eq. 5}$$

Figure 17:
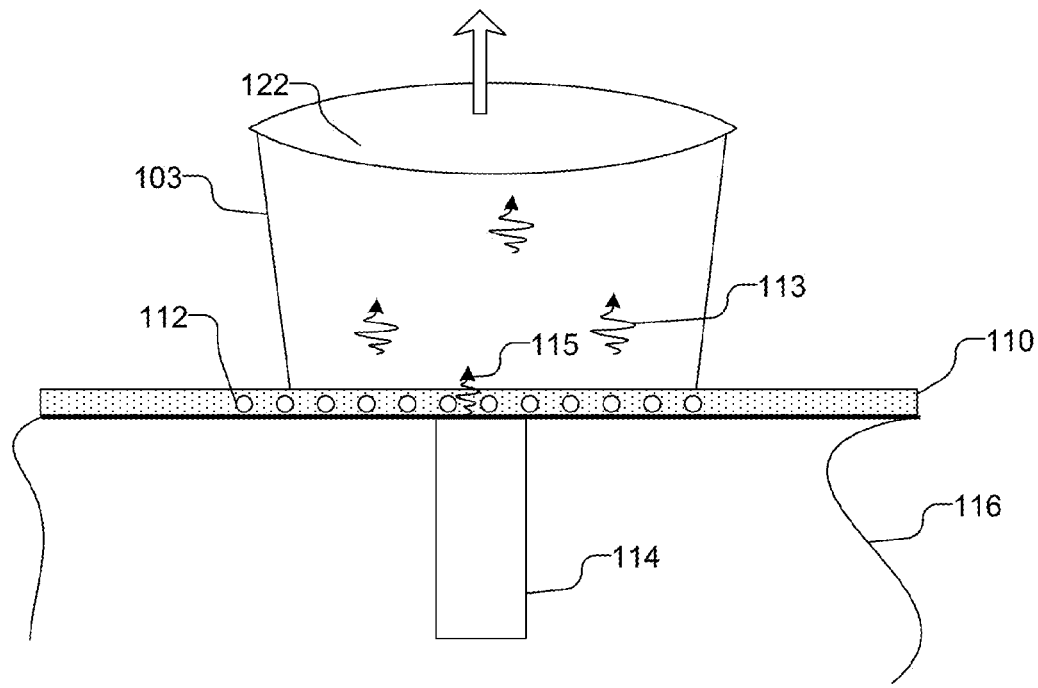
FIG. 17 schematically illustrates a crystal film with a plurality of nitrogen vacancy centers with a relatively high average density to detect the integral photoluminescence quenching caused by a photon emitter on a recording head as a function of bias current.

FIG. 17, by way of example, illustrates the detection of the quenching of the intensity of the photoluminescence caused by a near field photon emitter 114 by detecting integrated photoluminescence as a function of bias current. As illustrated in FIG. 17, the NV centers 112 in the crystal film 110 have a relatively high average density, e.g., the average distance d between adjacent nitrogen vacancy centers is less than two times a FWHM of the expected quenching profile. The density of NV centers may be chosen so that a plurality of NV centers, e.g. 10×10 NV centers, is located within the expected quenching area. The crystal film 110 may be placed in contact with the photon emitter 114, e.g., by being placed in contact with the ABS of the recording head 116. As discussed above in FIGS. 2A and 2B, the surface of the crystal film 110 may be patterned to form protruding islands, e.g., having a diameter that may be slightly larger than the maximum dimension of the expected quenching profile. As illustrated, the excitation illumination 103 may be wide-field illumination that is incident on the crystal film 110 and resulting photoluminescence is collected by lens 122 from an area of the crystal film 110 that is larger than the maximum expected quenching area. Wide field illumination, as used herein, refers to illumination used with microscopy having a homogeneously illuminated field of view to form an image, as compared to scanning a focused beam. The photoluminescence 113 is collected with and without the near field illumination 115 from the photon emitter 114 to detect the intensity $Int_{STED}$ of the integral photoluminescence quenching. The intensity $Int_{STED}$ of the integral photoluminescence quenching is measured as a function of the bias current $I_{Laser}$ supplied to the photon emitter. The measured intensity $Int_{STED}$ of the integral photoluminescence quenching that is a function of bias current $I_{Laser}$ may then be analyzed, e.g., by fitting to a photoluminescence quenching model at is a function of the bias current $I_{Laser}$ and power scaling factor F, or comparing to a library of data, which may be produced using the model or empirically, as discussed above, to determine characteristics of the photon emitter, such as the width of the near field illumination profile and the power scaling factor F.

Figure 18:
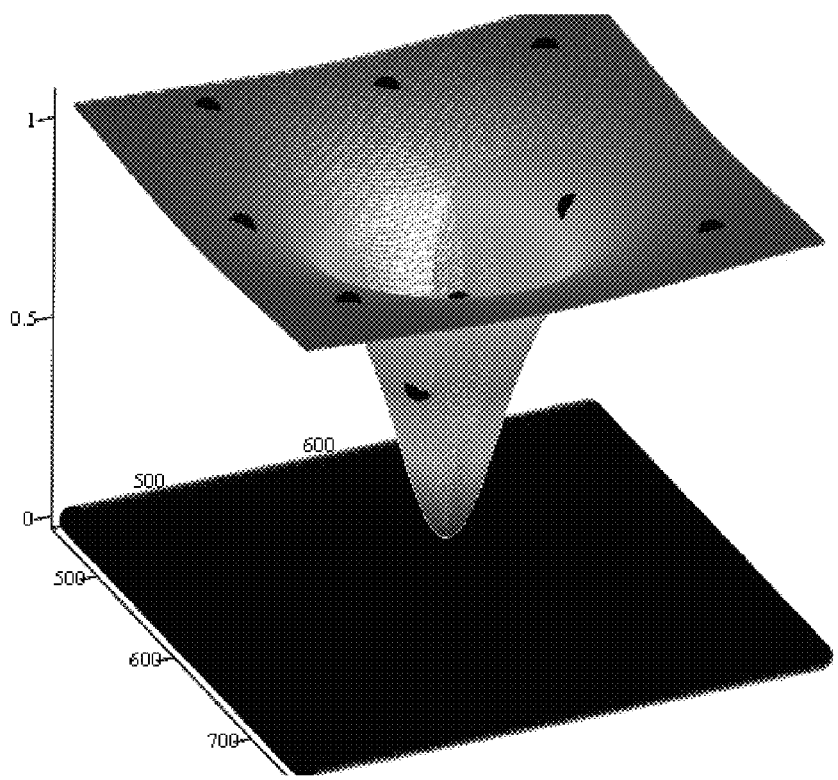
FIG. 18 is a three-dimensional graph illustrating the integral photoluminescence quenching with respect to position in two dimensions.

FIG. 18, by way of example, is a three-dimensional graph illustrating spatially resolved photoluminescence quenching intensity vs. x,y coordinates, where the spots indicate NV center locations where the photoluminescence quenching intensity is sampled. In case of wide-field imaging, the measured quantity is the integral $Int_{STED}$ over x and y of the quenching distribution. The quenching profile model for the integral photoluminescence quenching as a function of bias current may be written as:

$$Int_{STED}(I_{Laser}) = \qquad \text{eq. 6}$$
$$m \int_y \int_x \left[ \frac{FI_{Laser}}{4[(x-x_0)^2 + (y-y_0)^2]w^{-2} + 1} - I_0 \right]^n dx\, dy$$

where $I_{Laser}$ is the light source bias current, F and w are fitting parameters of the power scaling factor and the FWHM, respectively, m is the quenching scaling factor and n the quenching exponent, as discussed above. As discussed above with reference to equation 1, the factors m, n, and $I_o$ may be calibrated as previously discussed. Additionally, the calibration may be used to determine a power scaling factor F to calculate the light intensity $I=I_{Laser}*F$ of the device under test with $I_{Laser}$ being the bias current supplied to the light source. As can best be seen in eq. 6, the scaling factor F and the FWHM of the near field distribution w are independent parameters and hence can be fitted to the data. The measured intensity $Int_{STED}$ of the integral photoluminescence quenching depends on the intensity $P=F\, I_{Laser}$ of the light source under test. Because the characteristic coefficients m, $I_0$, const, and n are known from calibration, the power scaling factor F can be determined by the data fit.

Figure 19:
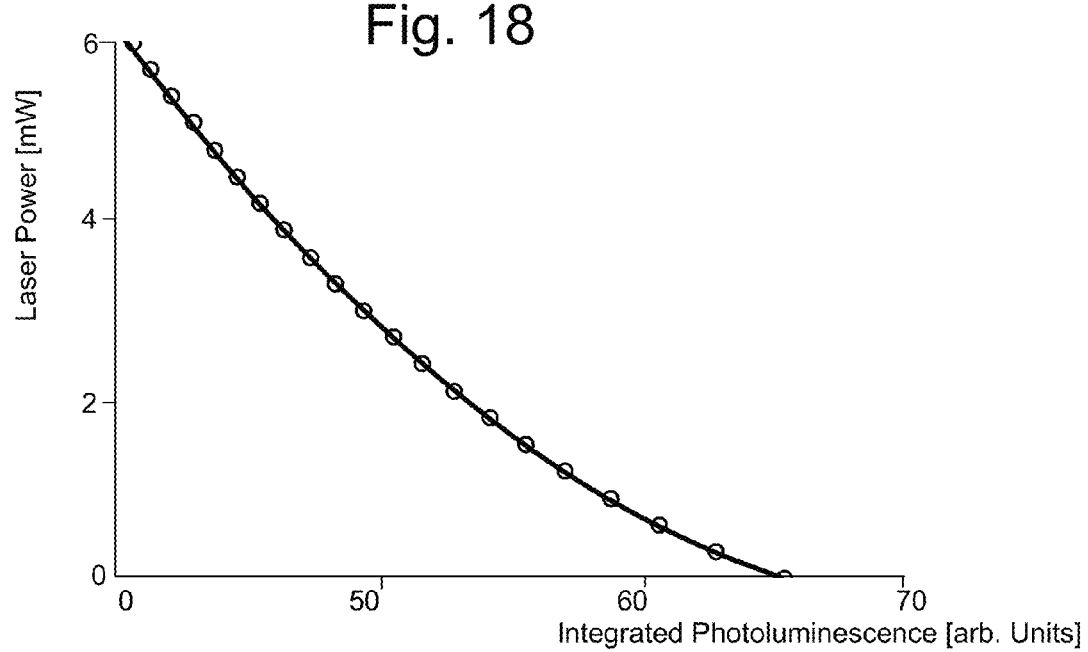
FIG. 19 illustrates a plot of detected integral photoluminescence quenching with respect to the laser (light source) power in mW.

The independent variable of the measurement is the bias-current $I_{Laser}$ supplied to the photon emitter under test. The amount of photoluminescence quenching is dependent on the light intensity generated by the photon emitter. Consequently, for the wide-field measurement of the quenching of the integrated photoluminescence, the data may be plotted as $Int_{STED}(I_{Laser})$ vs. $I_{Laser}$ or $Int_{STED}(I_{Laser})$ vs. $P=F\, I_{Laser}$, i.e., by rescaling with the fitting parameter F. FIG. 19, by way of example, illustrates a plot of the detected integral photoluminescence quenching $Int_{STED}(I_{Laser})$ with respect to the laser power P in mW, where $P=F\, I_{Laser}$. The line through the points in FIG. 19 is the determined fit to the integral photoluminescence quenching model, using fitting parameters w=28.762 of the near field illumination profile and power scaling factor F=2.037.

By determining the characteristics of the photon emitter, e.g., the peak power or power conversion factor and the aperture diameter determined, a finished photon emitter may be verified. For example, where the photon emitter is on a recording head, e.g., a HAMR head, each finished slider (or a sampling of finished sliders) may be verified by comparing the determined characteristics to an acceptable threshold. Recording heads with photon emitters having a peak power, a power conversion factor, or aperture diameter that is not within acceptable levels may be rejected.

Additionally, the characteristics of the photon emitter may be used in the process of attaching photon emitters to sliders, in the case of a HAMR head, or other types of devices. For example, the characteristics of the photon emitter, e.g., peak power, may be detected while actively aligning the photon emitter to the slider, thereby enabling an optimum alignment between the photon emitter and the slider, or other types of devices.

Additionally, the photon emitter discussed herein is a near field illumination source, such as the type used in recording heads. However, if desired, other near field illumination photon emitters may be tested, including optical fibers, plasmon tips for optical near field microscopy (SNOM), nano-photonics devices, optical wave-guides, laser-diodes, laser focal spot (beam waist) characterization. Moreover, it is possible to measure characteristics of far field emitters, such as a laser or fiber optics. For example, the process may be used to profile a laser beam produced by a laser or characterize fiber optics with a high degree of precision, i.e., on a nanometer length scale.

Although the present invention is illustrated in connection with specific embodiments for instructional purposes, the present invention is not limited thereto. Various adaptations and modifications may be made without departing from the scope of the invention. Therefore, the spirit and scope of the appended claims should not be limited to the foregoing description.

What is claimed is:

1. A method of determining one or more characteristics of a photon emitter, the method comprising:
   producing excitation illumination that is incident on a crystal film with one or more nitrogen vacancy centers, wherein the one or more nitrogen vacancy centers produces photoluminescence with an intensity in response to the excitation illumination;
   producing illumination from the photon emitter, wherein the photon emitter is an optical device with a near-field aperture on a recording head, the illumination being incident on the crystal film with the one or more nitrogen vacancy centers, wherein the illumination produced by the photon emitter quenches the intensity of the photoluminescence from the one or more nitrogen vacancy centers;
   detecting an amount of quenching of the intensity of the photoluminescence from the one or more nitrogen vacancy centers caused by the illumination of the photon emitter; and
   analyzing the amount of quenching of the intensity of the photoluminescence to determine the one or more characteristics of the photon emitter.

2. The method of claim 1, wherein analyzing the amount of quenching of the intensity of the photoluminescence comprises fitting the amount of quenching of the intensity of the photoluminescence to a photoluminescence quenching model to determine the one or more characteristics of the photon emitter.

3. The method of claim 1, wherein analyzing the amount of quenching of the intensity of the photoluminescence comprises comparing the amount of quenching of the intensity of the photoluminescence to a library of data to determine the one or more characteristics of the photon emitter.

4. The method of claim 1, wherein the illumination produced by the photon emitter is near field illumination.

5. The method of claim 1, wherein detecting the amount of quenching of the intensity of the photoluminescence from the one or more nitrogen vacancy centers of the crystal film comprises:
   detecting a first photoluminescence intensity from the one or more nitrogen vacancy centers in response to the excitation illumination without the illumination produced by the photon emitter incident on the crystal film;
   detecting a second photoluminescence intensity from the one or more nitrogen vacancy centers in response to the excitation illumination with the illumination produced by the photon emitter incident on the crystal film; and
   determining the amount of quenching of the intensity of the photoluminescence based on a difference between the first photoluminescence intensity and the second photoluminescence intensity.

6. The method of claim 1, wherein the method further comprises calibrating the photoluminescence quenching model by detecting a quenching scaling factor and a quenching exponent.

7. The method of claim 1, wherein the crystal film is on a probe tip, the method further comprising:
   scanning the crystal film on the probe tip over the photon emitter while detecting the quenching of the intensity of the photoluminescence to produce a one-dimensional distribution profile of the quenching of the intensity of the photoluminescence or a two-dimensional distribution profile of the quenching of the intensity of the photoluminescence;
   wherein analyzing the quenching of the intensity of the photoluminescence produces a peak power and a width of an illumination profile produced by the photon emitter.

8. The method of claim 7, wherein when the two-dimensional distribution profile of the quenching of the intensity of the photoluminescence is produced, a line extending through a point of greatest quenching of the two-dimensional distribution profile is used as a line profile of the quenching of the intensity of the photoluminescence, and wherein analyzing the quenching of the intensity of the photoluminescence uses the line profile of the quenching of the photoluminescence.

9. The method of claim 1, wherein the crystal film comprises a plurality of nitrogen vacancy centers, wherein an average distance between adjacent nitrogen vacancy centers is equal to or greater than two times a width of an expected quenching profile, the method further comprising:
   producing relative movement between the photon emitter and the crystal film thereby scanning the crystal film over the photon emitter while detecting the quenching of the intensity of the photoluminescence to produce a two-dimensional distribution profile of the quenching of the intensity of the photoluminescence;
   wherein analyzing the quenching of the intensity of the photoluminescence produces a peak power and a width of an illumination profile produced by the photon emitter.

10. The method of claim 9, wherein the photon emitter is on a recording head and the crystal film is in contact with an air bearing surface (ABS) of the recording head.

11. The method of claim 9, a line extending through a point of greatest quenching of the two-dimensional distribution profile is used as a line profile of the quenching of the intensity of the photoluminescence, and wherein analyzing the quenching of the intensity of the photoluminescence uses the line profile of the quenching of the photoluminescence.

12. The method of claim 1, wherein the crystal film comprises a plurality of nitrogen vacancy centers, wherein an average distance between adjacent nitrogen vacancy centers is less than two times a width of an expected quenching profile, the method further comprising:

producing a Stimulated Emission Depletion (STED) illumination that is coincident on the crystal film with the excitation illumination; and
scanning the excitation illumination and the STED illumination in two dimensions over the crystal film while detecting the quenching of the intensity of the photoluminescence to produce a two-dimensional distribution profile of the quenching of the intensity of the photoluminescence;
wherein analyzing the quenching of the intensity of the photoluminescence produces a peak power and a width of an illumination profile produced by the photon emitter.

13. The method of claim 12, a line extending through a point of greatest quenching of the two-dimensional distribution profile is used as a line profile of the quenching of the intensity of the photoluminescence, and wherein analyzing the quenching of the intensity of the photoluminescence uses the line profile of the quenching of the photoluminescence.

14. A method of determining one or more characteristics of a photon emitter, the method comprising:
producing excitation illumination that is incident on a crystal film with one or more nitrogen vacancy centers, wherein the one or more nitrogen vacancy centers produces photoluminescence with an intensity in response to the excitation illumination;
producing illumination from the photon emitter, the illumination being incident on the crystal film with the one or more nitrogen vacancy centers, wherein the illumination produced by the photon emitter quenches the intensity of the photoluminescence from the one or more nitrogen vacancy centers;
detecting an amount of quenching of the intensity of the photoluminescence from the one or more nitrogen vacancy centers caused by the illumination of the photon emitter;
analyzing the amount of quenching of the intensity of the photoluminescence to determine the one or more characteristics of the photon emitter; and
providing different magnitudes of a bias current to the photon emitter, wherein the one or more characteristics of the photon emitter are determined for the different magnitudes of the bias current.

15. A method of determining one or more characteristics of a photon emitter, the method comprising:
producing excitation illumination that is incident on a crystal film with one or more nitrogen vacancy centers, wherein the one or more nitrogen vacancy centers produces photoluminescence with an intensity in response to the excitation illumination;
producing illumination from the photon emitter, the illumination being incident on the crystal film with the one or more nitrogen vacancy centers, wherein the illumination produced by the photon emitter quenches the intensity of the photoluminescence from the one or more nitrogen vacancy centers;
detecting an amount of quenching of the intensity of the photoluminescence from the one or more nitrogen vacancy centers caused by the illumination of the photon emitter; and
analyzing the amount of quenching of the intensity of the photoluminescence to determine the one or more characteristics of the photon emitter;
wherein the crystal film has a patterned surface forming islands with a diameter larger than a maximum dimension of an expected quenching profile for the photon emitter.

16. A method of determining one or more characteristics of a photon emitter, the method comprising:
producing excitation illumination that is incident on a crystal film with one or more nitrogen vacancy centers, wherein the one or more nitrogen vacancy centers produces photoluminescence with an intensity in response to the excitation illumination;
producing illumination from the photon emitter, the illumination being incident on the crystal film with the one or more nitrogen vacancy centers, wherein the illumination produced by the photon emitter quenches the intensity of the photoluminescence from the one or more nitrogen vacancy centers;
detecting an amount of quenching of the intensity of the photoluminescence from the one or more nitrogen vacancy centers caused by the illumination of the photon emitter; and
analyzing the amount of quenching of the intensity of the photoluminescence to determine the one or more characteristics of the photon emitter;
wherein the crystal film comprises a plurality of nitrogen vacancy centers, wherein an average distance between adjacent nitrogen vacancy centers is less than two times a width of an expected quenching profile, wherein detecting the quenching of the intensity of the photoluminescence comprises collecting the quenching of the intensity of the photoluminescence from an area on the crystal film that is larger than the expected quenching profile, the method further comprising:
providing different magnitudes of a bias current to the photon emitter, wherein the quenching of the intensity of the photoluminescence is detected as a function of the bias current;
wherein analyzing the quenching of the intensity of the photoluminescence produces a bias current to power conversion factor and a width of an illumination profile produced by the photon emitter.

17. A method of determining one or more characteristics of a photon emitter, the method comprising:
producing a first excitation illumination that is incident on a crystal film with one or more nitrogen vacancy centers, wherein the one or more nitrogen vacancy centers produces photoluminescence with an intensity in response to the first excitation illumination;
detecting a first photoluminescence intensity from the one or more nitrogen vacancy centers in response to the first excitation illumination;
producing a second excitation illumination that is incident on the crystal film with the one or more nitrogen vacancy centers;
producing illumination from the photon emitter, the illumination being incident on the crystal film with the one or more nitrogen vacancy centers, wherein the illumination produced by the photon emitter quenches the intensity of the photoluminescence produced by the one or more nitrogen vacancy centers in response to the second excitation illumination;
detecting a second photoluminescence intensity from the one or more nitrogen vacancy centers in response to the second excitation illumination and the illumination produced by the photon emitter;
determining an amount of quenching of photoluminescence intensity based on a difference between the first photoluminescence intensity and the second photoluminescence intensity; and analyzing the amount of quenching of the intensity of the photoluminescence to determine the one or more characteristics of the photon emitter.

18. The method of claim 17, wherein analyzing the amount of quenching of the intensity of the photoluminescence comprises fitting the amount of quenching of the intensity of the photoluminescence to a photoluminescence quenching model to determine the one or more characteristics of the photon emitter.

19. The method of claim 17, wherein analyzing the amount of quenching of the intensity of the photoluminescence comprises comparing the amount of quenching of the intensity of the photoluminescence to a library of data to determine the one or more characteristics of the photon emitter.

20. The method of claim 17, the method further comprising providing different magnitudes of a bias current to the photon emitter, wherein the one or more characteristics of the photon emitter are determined for the different magnitudes of the bias current.

21. The method of claim 17, wherein the photon emitter is a optical device with a near-field aperture on a recording head.

22. The method of claim 17, wherein analyzing the quenching of the intensity of the photoluminescence produces a peak power and a width of an illumination profile produced by the photon emitter.

23. The method of claim 22, wherein the crystal film is on a probe tip, the method further comprising:
    scanning the crystal film on the probe tip over the photon emitter while detecting the quenching of the intensity of the photoluminescence to produce a one-dimensional distribution profile of the quenching of the intensity of the photoluminescence or a two-dimensional distribution profile of the quenching of the intensity of the photoluminescence; and
    determining a line extending through a point of greatest quenching of the two-dimensional distribution profile when two-dimensional distribution profile of the quenching of the intensity of the photoluminescence is produced, the line is used as a line profile of the quenching of the intensity of the photoluminescence, and wherein analyzing the quenching of the intensity of the photoluminescence uses the line profile of the quenching of the photoluminescence.

24. The method of claim 22, wherein the crystal film comprises a plurality of nitrogen vacancy centers, wherein an average distance between adjacent nitrogen vacancy centers is equal to or greater than two times a width of an expected quenching profile, the method further comprising:
    producing relative movement between the photon emitter and the crystal film thereby scanning the crystal film over the photon emitter while detecting the quenching of the intensity of the photoluminescence to produce a two-dimensional distribution profile of the quenching of the intensity of the photoluminescence; and
    determining a line extending through a point of greatest quenching of the two-dimensional distribution profile that is a line profile of the quenching of the intensity of the photoluminescence, and wherein analyzing the quenching of the intensity of the photoluminescence uses the line profile of the quenching of the photoluminescence.

25. The method of claim 22, wherein the crystal film comprises a plurality of nitrogen vacancy centers, wherein an average distance between adjacent nitrogen vacancy centers is less than two times a width of an expected quenching profile, the method further comprising:
    producing a Stimulated Emission Depletion (STED) illumination that is coincident on the crystal film with excitation illumination; and
    scanning the coincident excitation illumination and the STED illumination in two dimensions over the crystal film while detecting the quenching of the intensity of the photoluminescence to produce a two-dimensional distribution profile of the quenching of the intensity of the photoluminescence; and
    determining a line extending through a point of greatest quenching of the two-dimensional distribution profile that is a line profile of the quenching of the intensity of the photoluminescence, and wherein analyzing the quenching of the intensity of the photoluminescence uses the line profile of the quenching of the photoluminescence.

26. The method of claim 17, wherein the crystal film comprises a plurality of nitrogen vacancy centers, wherein an average distance between adjacent nitrogen vacancy centers is less than two times a width of an expected quenching profile, wherein detecting the quenching of the intensity of the photoluminescence comprises collecting the quenching of the intensity of the photoluminescence from an area on the crystal film that is larger than the expected quenching profile, the method further comprising:
    providing different magnitudes of a bias current to the photon emitter, wherein the quenching of the intensity of the photoluminescence is detected as a function of the bias current;
    wherein analyzing the quenching of the intensity of the photoluminescence produces a bias current to power conversion factor and a width of an illumination profile produced by the photon emitter.

27. An apparatus for determining one or more characteristics of a photon emitter, the apparatus comprising:
    a light source that produces excitation illumination that is incident on a crystal film with one or more nitrogen vacancy centers, wherein the one or more nitrogen vacancy centers produces photoluminescence with an intensity in response to the excitation illumination;
    a microscope configured to detect the photoluminescence produced by the nitrogen vacancy centers in response to the excitation illumination;
    a bias source configured to provide bias signals;
    a probe card coupled to the bias source and configured to be connected to a device that includes the photon emitter, the probe card provides a bias signal to the device that causes the photon emitter to emit illumination that is incident on the crystal film with the one or more nitrogen vacancy centers, wherein the illumination produced by the photon emitter quenches the intensity of the photoluminescence from the one or more nitrogen vacancy centers; and
    a processor coupled to control the microscope, the light source and the bias source and configured to cause the microscope to detect the photoluminescence produced by the nitrogen vacancy centers in response to the excitation illumination and to determine an amount of quenching of the intensity of the photoluminescence from the one or more nitrogen vacancy centers caused by the illumination produced by the photon emitter, and to analyze the amount of quenching of the intensity of the photoluminescence to determine the one or more characteristics of the photon emitter.

28. The apparatus of claim 27, wherein the processor is configured to analyze the amount of quenching of the intensity of the photoluminescence by being configured to fit the amount of quenching of the intensity of the photoluminescence to a photoluminescence quenching model to determine the one or more characteristics of the photon emitter.

29. The apparatus of claim 27, wherein the processor is configured to analyze the amount of quenching of the intensity of the photoluminescence by being configured to compare the amount of quenching of the intensity of the photoluminescence to a library of data to determine the one or more characteristics of the photon emitter.

30. The apparatus of claim 27, wherein the processor is configured to determine the amount of quenching of the intensity of the photoluminescence from the one or more nitrogen vacancy centers of the crystal film by being configured to:
cause the microscope to detect a first photoluminescence intensity from the one or more nitrogen vacancy centers in response to the excitation illumination without the illumination produced by the photon emitter incident on the crystal film;
cause the microscope to detect a second photoluminescence intensity from the one or more nitrogen vacancy centers in response to the excitation illumination with the illumination produced by the photon emitter incident on the crystal film;
wherein the amount of quenching of the intensity of the photoluminescence is determined based on a difference between the first photoluminescence intensity and the second photoluminescence intensity.

31. The apparatus of claim 27, wherein the processor is configured to cause the bias source to provide different magnitudes of a bias current to the device, wherein the one or more characteristics of the photon emitter are determined for the different magnitudes of the bias current.

32. The apparatus of claim 27, wherein the photon emitter is a optical device with a near-field aperture on a recording head.

33. The apparatus of claim 27, wherein the crystal film has a patterned surface forming islands with a diameter larger than a maximum dimension of an expected quenching profile for the photon emitter.

34. The apparatus of claim 27, wherein the processor is configured to analyze the quenching of the intensity of the photoluminescence to determine a peak power and a width of an illumination profile produced by the photon emitter.

35. The apparatus of claim 34, further comprising:
a probe having a probe tip holding the crystal film;
wherein the processor is coupled to the probe and causes the probe to scan the crystal film on the probe tip over the photon emitter while the microscope detects the photoluminescence to produce a one-dimensional distribution profile of the quenching of the intensity of the photoluminescence or a two-dimensional distribution profile of the quenching of the intensity of the photoluminescence;
wherein the processor is further configured to determine a line extending through a point of greatest quenching of the two-dimensional distribution profile when the two-dimensional distribution profile of the quenching of the intensity of the photoluminescence is produced, the line is used as a line profile of the quenching of the intensity of the photoluminescence, and wherein the processor is configured to analyze the quenching of the intensity of the photoluminescence using the line profile of the quenching of the photoluminescence.

36. The apparatus of claim 34, wherein the crystal film comprises a plurality of nitrogen vacancy centers, wherein an average distance between adjacent nitrogen vacancy centers is equal to or greater than two times a width of an expected quenching profile, the apparatus further comprising:
at least one actuator to produce relative movement between the photon emitter and the crystal film thereby scanning the crystal film over the photon emitter while the microscope detects the photoluminescence to produce a two-dimensional distribution profile of the quenching of the intensity of the photoluminescence; and
wherein the processor is further configured to determine a line extending through a point of greatest quenching of the two-dimensional distribution profile that is a line profile of the quenching of the intensity of the photoluminescence, and wherein the processor is configured to analyze the quenching of the intensity of the photoluminescence using the line profile of the quenching of the photoluminescence.

37. The apparatus of claim 34, wherein the crystal film comprises a plurality of nitrogen vacancy centers, wherein an average distance between adjacent nitrogen vacancy centers is less than two times a width of an expected quenching profile, the apparatus further comprising:
a second light source that produces depletion illumination that is coincident on the crystal film with the excitation illumination;
at least one mirror to scan the coincident excitation illumination and the depletion illumination in two dimensions over the crystal film while the microscope detects the photoluminescence to produce a two-dimensional distribution profile of the quenching of the intensity of the photoluminescence;
wherein the processor is further configured to determine a line extending through a point of greatest quenching of the two-dimensional distribution profile that is a line profile of the quenching of the intensity of the photoluminescence, and wherein the processor is configured to analyze the quenching of the intensity of the photoluminescence using the line profile of the quenching of the photoluminescence.

38. The apparatus of claim 27, wherein the crystal film comprises a plurality of nitrogen vacancy centers, wherein an average distance between adjacent nitrogen vacancy centers is less than two times a width of an expected quenching profile, wherein the microscope detects the photoluminescence from an area on the crystal film that is larger than the expected quenching profile, and wherein the processor is configured to determine the quenching of the intensity of the photoluminescence comprises over the area on the crystal film, wherein the processor is further configured to:
cause the bias source provide different magnitudes of bias currents to the device, wherein the quenching of the intensity of the photoluminescence is determined as a function of bias current;
wherein the processor is configured to analyze the quenching of the intensity of the photoluminescence to determine a bias current to power conversion factor and a width of an illumination profile produced by the photon emitter.

* * * * *